(12) United States Patent
Renold et al.

(10) Patent No.: US 8,859,592 B2
(45) Date of Patent: *Oct. 14, 2014

(54) INSECTICIDAL COMPOUNDS

(71) Applicant: Syngenta Crop Protection LLC, Greensboro, NC (US)

(72) Inventors: Peter Renold, Stein (CH); Jerome Yves Cassayre, Stein (CH); Jagadish Pabba, Goa (IN); Myriem El Qacemi, Stein (CH); Thomas Pitterna, Stein (CH)

(73) Assignee: Syngenta Corp Protection LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/891,660

(22) Filed: May 10, 2013

(65) Prior Publication Data
US 2013/0245072 A1   Sep. 19, 2013

Related U.S. Application Data

(63) Continuation of application No. 13/145,689, filed as application No. PCT/EP2010/050358 on Jan. 13, 2010, now abandoned.

(30) Foreign Application Priority Data

Jan. 22, 2009   (IN) ............................ 127/DELP/2009
Jun. 22, 2009   (GB) .................................. 0910767.3
Jul. 24, 2009   (WO) ................. PCT/EP2009/059563

(51) Int. Cl.
| A01N 43/80 | (2006.01) |
| A01N 43/82 | (2006.01) |
| C07D 413/10 | (2006.01) |
| C07D 413/14 | (2006.01) |
| C07D 417/10 | (2006.01) |
| C07D 417/14 | (2006.01) |
| C07D 417/04 | (2006.01) |
| C07D 413/04 | (2006.01) |

(52) U.S. Cl.
CPC .............. *A01N 43/80* (2013.01); *C07D 417/04* (2013.01); *C07D 413/10* (2013.01); *C07D 417/14* (2013.01); *C07D 413/14* (2013.01); *C07D 417/10* (2013.01); *A01N 43/82* (2013.01); *C07D 413/04* (2013.01)
USPC ........... 514/338; 514/362; 514/375; 514/378; 546/268.7; 548/126; 548/217; 548/240

(58) Field of Classification Search
None
See application file for complete search history.

(56) References Cited

FOREIGN PATENT DOCUMENTS

| WO | 2007/079162 A1 | 7/2007 |
| WO | 2008/154528 A2 | 12/2008 |
| WO | 2010/020522 A1 | 2/2010 |

*Primary Examiner* — Janet L Andres
*Assistant Examiner* — Timothy R Rozof
(74) *Attorney, Agent, or Firm* — Brian D. McAlhaney

(57) ABSTRACT

A compound of formula (I):

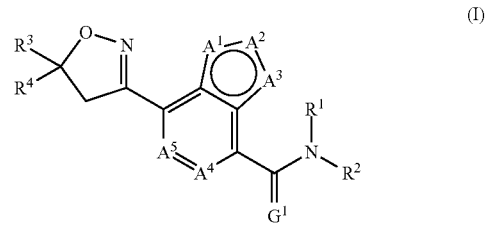

wherein $A^1$, $A^2$, $A^3$, $A^4$, $A^5$, $G^1$, $R^1$, $R^2$, $R^3$ and $R^4$ are as defined in claim 1; or a salt or N-oxide thereof.

Furthermore, the present invention relates to processes and intermediates for preparing compounds of formula (I), to insecticidal, acaricidal, nematicidal and molluscicidal compositions comprising them and to methods of using them to combat and control insect, acarine, nematode and mollusc pests.

16 Claims, No Drawings

INSECTICIDAL COMPOUNDS

This application is continuation of U.S. application Ser. No. 13/145,689, filed Jun. 21, 2011, which is a 371 of International Application No. PCT/EP2010/050358, filed Jan. 13, 2010, which claims priority to 127/DELNP/2009, filed Jan. 22, 2009, GB 0910767.3, filed Jun. 22, 2009, and PCT/EP2009/059563, filed Jul. 24, 2009, the contents of which are incorporated herein by reference.

The present invention relates to certain benzamide isoxazolines, to processes and intermediates for preparing them, to insecticidal, acaricidal, nematicidal and molluscicidal compositions comprising them and to methods of using them to combat and control insect, acarine, nematode and mollusc pests.

Certain bicyclic isoxazoline derivatives with insecticidal properties are disclosed, for example, in WO 2007/079162, WO 2008/154528 and WO 2009/002809.

It has now surprisingly been found that certain isoxazoline-substituted bicyclic heteroaromatic compounds have insecticidal properties.

The present invention therefore provides a compound of formula (I)

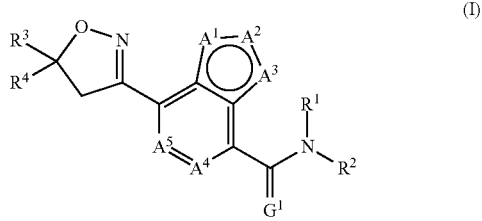

wherein
$A^1$, $A^2$ and $A^3$ are independently C—$R^5$, nitrogen, N—$R^6$, oxygen or sulfur, provided that two of $A^1$, $A^2$ or $A^3$ are C—$R^5$ or nitrogen and that one of $A^1$, $A^2$ or $A^3$ is N—$R^6$, oxygen or sulfur;
$A^4$ and $A^5$ are independently C—$R^5$ or nitrogen;
$G^1$ is oxygen or sulfur;
$R^1$ is hydrogen, $C_1$-$C_8$alkyl, $C_1$-$C_8$alkylcarbonyl-, or $C_1$-$C_8$alkoxycarbonyl-;
$R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one to five $R^8$, aryl-$C_1$-$C_4$alkylene- or aryl-$C_1$-$C_4$alkylene- wherein the aryl moiety is substituted by one to five $R^9$, heterocyclyl-$C_1$-$C_4$alkylene- or heterocyclyl-$C_1$-$C_4$alkylene- wherein the heterocyclyl moiety is substituted by one to five $R^9$, aryl or aryl substituted by one to five $R^9$, heterocyclyl or heterocyclyl substituted by one to five $R^9$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene;
$R^3$ is $C_1$-$C_8$haloalkyl;
$R^4$ is aryl or aryl substituted by one to five $R^{10}$, or heteroaryl or heteroaryl substituted by one to five $R^{10}$;
each $R^5$ is independently hydrogen, halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^6$ is independently hydrogen or $C_1$-$C_8$alkyl;
each $R^7$ is independently halogen, cyano, nitro, hydroxy, $C_1$-$C_8$alkoxy, $C_1$-$C_8$haloalkoxy, mercapto, $C_1$-$C_8$alkylthio-, $C_1$-$C_8$haloalkylthio-; $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^8$ is independently halogen or $C_1$-$C_8$alkyl;
each $R^9$ and $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{11}$, or heterocyclyl or heterocyclyl substituted by one to five $R^{11}$; and
each $R^{11}$ is independently halogen, cyano, nitro, $C_1$-$C_4$alkyl, $C_1$-$C_4$haloalkyl, $C_1$-$C_4$alkoxy, or $C_1$-$C_4$haloalkoxy; or a salt or N-oxide thereof;
provided that -$A^1$-$A^2$-$A^3$- is not —O—(CR$^5$)═N—, —S—(CR$^5$)═N—, N═(CR$^5$)—O— or —N═(CR$^5$)—S— irrespective of the values for $A^4$ and $A^5$, and
provided that -$A^1$-$A^2$-$A^3$- is not —(CR$^5$)═(CR$^5$)—O—, —O—(CR$^5$)═(CR$^5$)—, —(CR$^5$)═(CR$^5$)—S—, —S—(CR$^5$)═(CR$^5$)—, —(CR$^5$)═(CR$^5$)—(NR$^6$)—, —(NR$^6$)—(CR$^5$)═(CR$^5$)—, —(CR$^5$)═N—(NR$^6$)— and —(NR$^6$)—N═(CR$^5$)— when $A^4$ and $A^5$ are both C—$R^5$.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, at the —CR$^3$R$^4$— group, and may exist as enantiomers (or as pairs of diastereoisomers) or as mixtures of such.

Alkyl groups (either alone or as part of a larger group, such as alkoxy, alkylthio-, alkylsulfinyl-, alkylsulfonyl-, alkylcarbonyl-, or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, —CH$_2$—, —CH$_2$—CH$_2$—, —CH(CH$_3$)—, —CH$_2$—CH$_2$—CH$_2$—, —CH(CH$_3$)—CH$_2$—, or —CH(CH$_2$CH$_3$)—. The alkylene groups are preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy, haloalkylthio-, haloalkylsulfinyl- or haloalkylsulfonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene-) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene-) are aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl. Examples of bicyclic groups include quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups (either alone or as part of a larger group, such as heterocyclyl-alkylene-) are defined to include heteroaryl groups and in addition their unsaturated or partially unsaturated analogues. Examples of monocyclic groups include thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,3]dioxolanyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Preferred values of $A^1$, $A^2$, $A^3$, $A^4$, $A^5$, $G^1$, $R^1$, $R^2$, $R^3$, $R^4$, $R^5$, $R^6$, $R^7$, $R^8$, $R^9$, $R^{10}$ and $R^{11}$ are, in any combination, as set out below.

For the avoidance of doubt, the ring formed by $A^1$, $A^2$ and $A^3$ is an aromatic ring.

Preferably $A^1$ is nitrogen or N—$R^6$, most preferably nitrogen or N—$CH_3$.

Preferably $A^2$ is C—$R^5$, N—$R^6$, nitrogen or sulfur, more preferably $A^2$ is C—$R^5$, nitrogen or sulfur, most preferably nitrogen or sulfur.

Preferably $A^3$ is nitrogen or N—$R^6$, most preferably nitrogen or N—$CH_3$.

In one embodiment $A^1$ and $A^3$ are nitrogen or N—$R^6$ and $A^2$ is C—$R^5$, N—$R^6$, nitrogen or sulfur, more preferably $A^1$ and $A^3$ are nitrogen or N—$R^6$ and $A^2$ is N—$R^6$, nitrogen or sulfur, more preferably $A^1$ and $A^3$ are nitrogen and $A^2$ is N—$R^6$ or sulfur. For example, -$A^1$-$A^2$-$A^3$- may be selected from =N—S—N=, —N=C($R^5$)—N($R^6$)—, —N($R^6$)—C($R^5$)=N—, =N—N($R^6$)—N=, —N=N—N($R^6$)— and —N($R^6$)—N=N—, more preferably =N—S—N=, —N=C($R^5$)—N($R^6$)—, =N—N($R^6$)—N=, and =N—N—N($R^6$)—, more preferably =N—S—N=, =N—N($R^6$)—N=, and —N=N—N($R^6$)—, most preferably =N—S—N=. In one embodiment two of $A^1$, $A^2$ and $A^3$ are nitrogen and the other of $A^1$, $A^2$ and $A^3$ is N—$R^6$, oxygen or sulfur, more preferably two of $A^1$, $A^2$ and $A^3$ are nitrogen and the other of $A^1$, $A^2$ and $A^3$ is N—$R^6$ or sulfur. For example, -$A^1$-$A^2$-$A^3$- may be selected from =N—S—N=, —S—N=N—, —N=N—S—, =N—N($R^6$)—N=, —N=N—N($R^6$)— and —N($R^6$)—N=N—, in particular from =N—S—N=, —N=N—N($R^6$)— and =N—N($R^6$)—N=. Preferably two of $A^1$, $A^2$ and $A^3$ are nitrogen and the other of $A^1$, $A^2$ and $A^3$ is sulfur. For example, -$A^1$-$A^2$-$A^3$- may be selected from =N—S—N=, —S—N=N—, and —N=N—S—. Most preferably -$A^1$-$A^2$-$A^3$- is =N—S—N=.

Preferably $A^4$ is C—$R^5$, most preferably C—H or C—$CH_3$, in particular C—H.

Preferably $A^5$ is C—$R^5$, most preferably C—H.

For example, $A^4$ and $A^5$ may each independently be C—H or nitrogen, more preferably $A^4$ and $A^5$ are both C—H.

Preferably $G^1$ is oxygen.

Preferably $R^1$ is hydrogen, methyl, ethyl, methylcarbonyl-, or methoxycarbonyl-, more preferably hydrogen, methyl or ethyl, even more preferably hydrogen or methyl, most preferably hydrogen.

Preferably $R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one to five $R^8$, aryl-$C_1$-$C_4$alkylene- or aryl-$C_1$-$C_4$alkylene- wherein the aryl moiety is substituted by one to five $R^9$, heterocyclyl-$C_1$-$C_4$alkylene- or heterocyclyl-$C_1$-$C_4$alkylene- wherein the heterocyclyl moiety is substituted by one to five $R^9$, aryl or aryl substituted by one to five $R^9$, heterocyclyl or heterocyclyl substituted by one to five $R^9$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxo-thietanyl, dioxo-thietanyl, pyrrolidinyl, tetrahydrofuranyl, [1,3]dioxolanyl, piperidinyl, piperazinyl, [1,4]dioxanyl, and morpholinyl, 2,3-dihydro-benzofuranyl, benzo[1,3]dioxolanyl, and 2,3-dihydro-benzo[1,4]dioxinyl.

Preferably $R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one to five $R^8$, aryl-$C_1$-$C_4$alkylene- or aryl-$C_1$-$C_4$alkylene- wherein the aryl moiety is substituted by one to five $R^9$, heterocyclyl-$C_1$-$C_4$alkylene- or heterocyclyl-$C_1$-$C_4$alkylene- wherein the heterocyclyl moiety is substituted by one to five $R^9$, aryl or aryl substituted by one to five $R^9$, heterocyclyl or heterocyclyl substituted by one to five $R^9$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from pyridyl, pyrazolyl, benzimidazolyl, furanyl, thiazolyl, oxetanyl, thietanyl, oxo-thietanyl and dioxo-thietanyl.

Preferably $R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one to five $R^8$, phenyl-$C_1$-$C_4$alkylene- or phenyl-$C_1$-$C_4$alkylene- wherein the phenyl moiety is substituted by one to five $R^9$, pyridyl-$C_1$-$C_4$alkylene- or pyridyl-$C_1$-$C_4$alkylene- wherein the pyridyl moiety is substituted by one to four $R^9$, imidazolyl-$C_1$-$C_4$alkylene or imidazolyl-$C_1$-$C_4$alkylene wherein the imidazolyl moiety is substituted by one to five $R^9$, oxetanyl or oxetanyl substituted by one to five $R^9$, thietanyl or thietanyl substituted by one to five $R^9$, oxo-thietanyl or oxo-thietanyl substituted by one to five $R^9$, dioxo-thietanyl or dioxo-thietanyl substituted by one to five $R^9$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene; for example $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one to five $R^8$, phenyl-$C_1$-$C_4$alkylene- or phenyl-$C_1$-$C_4$alkylene- wherein the phenyl moiety is substituted by one to five $R^9$, pyridyl-$C_1$-$C_4$alkylene- or pyridyl-$C_1$-$C_4$alkylene- wherein the pyridyl moiety is substituted by one to four $R^9$, oxetanyl or oxetanyl substituted by one to five $R^9$, thietanyl or thietanyl substituted by one to five $R^9$, oxo-thietanyl or oxo-thietanyl substituted by one to five $R^9$, or dioxo-thietanyl or dioxo-thietanyl substituted by one to five $R^9$.

Preferably $R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one or two methyl groups, phenyl-$C_1$-$C_4$alkylene- or phenyl-$C_1$-$C_4$alkylene- wherein the phenyl moiety is substituted by one to five $R^9$, pyridyl-$C_1$-$C_4$alkylene- or pyridyl-$C_1$-$C_4$alkylene- wherein the pyridyl moiety is substituted by one to four $R^9$, imidazolyl-$C_1$-$C_4$alkylene or imidazolyl-$C_1$-$C_4$alkylene wherein the imidazolyl moiety is substituted by one to five $R^9$, oxetanyl or oxetanyl substituted by one to five $R^9$, thietanyl or thietanyl substituted by one to five $R^9$, oxo-thietanyl or oxo-thietanyl substituted by one to five $R^9$, dioxo-thietanyl or dioxo-thietanyl substituted by one to five $R^9$, for example $C_1$-$C_8$alkyl, $C_3$-$C_{10}$cycloalkyl substituted by one or two methyl groups, phenyl-$C_1$-$C_4$alkylene- or phenyl-$C_1$-$C_4$alkylene- wherein the phenyl moiety is substituted by one to five $R^9$, pyridyl-$C_1$-$C_4$alkylene- or pyridyl-$C_1$-$C_4$alkylene- wherein the pyridyl moiety is substituted by one to four $R^9$, oxetanyl, thietanyl, oxo-thietanyl or dioxo-thietanyl.

Preferably $R^2$ is $C_3$-$C_6$alkyl or $C_3$-$C_6$alkyl substituted by one to five $R^7$, $C_4$-$C_8$cycloalkyl or $C_4$-$C_8$cycloalkyl substituted by one or two methyl groups, phenyl-$C_1$-$C_2$alkylene- or phenyl-$C_1$-$C_2$alkylene- wherein the phenyl moiety is substituted by one to five $R^9$, pyridyl-$C_1$-$C_2$alkylene- or pyridyl-$C_1$-$C_2$alkylene- wherein the pyridyl moiety is substituted by one to four $R^9$, imidazolyl-$C_1$-$C_2$alkylene- or imidazolyl-$C_1$-$C_2$alkylene- wherein the imidazolyl moiety is substituted by one to five $R^9$, oxetanyl or oxetanyl substituted by one to five $R^9$, thietanyl or thietanyl substituted by one to five $R^9$, oxo-thietanyl or oxo-thietanyl substituted by one to five $R^9$, dioxo-thietanyl or dioxo-thietanyl substituted by one to five $R^9$, more preferably $C_3$-$C_6$alkyl or $C_3$-$C_6$alkyl substituted by one to three $R^7$, $C_4$-$C_8$cycloalkyl, phenyl-methylene- or phenyl-methylene- wherein the phenyl moiety is substituted by one to three $R^9$, imidazolyl-methylene- or imidazolyl-methylene- wherein the imidazolyl moiety is substituted by one to three $R^9$, thietanyl or methylthietanyl, oxo-thietanyl or methyl-oxo-thietanyl, dioxo-thietanyl or methyl-dioxo-thietanyl, most preferably butyl, 2,2,2-trifluoroethyl, ethyl, 1-methoxy-prop-2-yl, (1H-benzimidazol-2-yl)-methyl, 3,3,3-trifluoro-propyl, phenyl-methyl-, (4-methoxy-phenyl)-methyl-, 2-methyl-1-methylthio-prop-2-yl, cyclobutyl, bicyclo[2.2.1]heptan-2-yl, thietanyl, methylthietanyl, oxo-thietanyl or dioxo-thietanyl, in particular thietanyl, oxo-thietanyl or dioxo-thietanyl.

A group of preferred compounds are those wherein $R^2$ is $C_1$-$C_6$alkyl or $C_1$-$C_6$alkyl substituted by one to five $R^7$, for example ethyl-, butyl-, but-2-yl-, 3-bromo-propyl-, 2,2,2-trifluoro-ethyl-, 3,3,3-trifluoro-propyl-, 2-methyl-1-methylthio-prop-2-yl, 2-methoxy-ethyl-, and 1-methoxy-prop-2-yl-, for example ethyl-, butyl-, but-2-yl-, 3-bromo-propyl-, 2,2,2-trifluoro-ethyl-, 3,3,3-trifluoro-propyl-, 2-methoxy-ethyl-, and 1-methoxy-prop-2-yl-.

A group of preferred compounds are those wherein $R^2$ is $C_3$-$C_8$cycloalkyl or $C_3$-$C_8$cycloalkyl substituted by one to five $R^8$, for example cyclobutyl-, bicyclo[2.2.1]heptan-2-yl and 2-methyl-cyclohex-1-yl-, for example cyclobutyl- and 2-methyl-cyclohex-1-yl-.

A group of preferred compounds are those wherein $R^2$ is aryl-$C_1$-$C_2$alkylene- or aryl-$C_1$-$C_2$alkylene- wherein the aryl moiety is substituted by one to five $R^9$, for example phenyl-methyl-, 1-phenyl-eth-1-yl-, 2-phenyl-eth-1-yl-, (3-chloro-phenyl)-methyl-, (2-fluoro-phenyl)-methyl-, (4-methoxy-phenyl)-methyl-, (2-trifluoromethyl-phenyl)-methyl- and (2-trifluoromethoxy-phenyl)-methyl-.

A group of preferred compounds are those wherein $R^2$ is heterocyclyl-$C_1$-$C_2$alkylene- or heterocyclyl-$C_1$-$C_2$alkylene- wherein the heterocyclyl moiety is substituted by one to five $R^9$, for example (pyrid-2-yl)-methyl-, (pyrid-3-yl)-methyl-, (2-chloro-pyrid-5-yl)-methyl-, (1-methyl-1H-imidazol-4-yl)-methyl-, (furan-2-yl)-methyl-, 2-(thiophen-2'-yl)-eth-1-yl-, 2-(indol-3'-yl)-eth-1-yl-, (1H-benzimidazol-2-yl)-methyl-, (oxetan-2-yl)-methyl-, (tetrahydro-furan-2-yl)-methyl-, 2-([1',3']-dioxolan-2'-yl)-eth-1-yl-, 2-(morpholin-4'-yl)-eth-1-yl-, 2-(benzo[1',3']dioxol-5'-yl)-eth-1-yl-, and (2,3-dihydro-benzo[1,4]dioxin-6-yl)-methyl-, more preferably $R^2$ is heteroaryl-$C_1$-$C_2$alkylene- or heteroaryl-$C_1$-$C_2$alkylene- wherein the heteroaryl moiety is substituted by one to five $R^9$.

A group of preferred compounds are those wherein $R^2$ is aryl or aryl substituted by one to five $R^9$, for example 2-chloro-phenyl-, 3-fluoro-phenyl-, 2-methyl-phenyl-, 2-chloro-6-methyl-phenyl-, 2-trifluoromethyl-phenyl-, and 2,4-dimethoxy-phenyl-.

A group of preferred compounds are those wherein $R^2$ is heterocyclyl or heterocyclyl substituted by one to five $R^9$, for example 3-methyl-pyrid-2-yl-, 1,3-dimethyl-1H-pyrazol-5-yl-, 4-methyl-thiazol-2-yl-, 5-methyl-thiadiazol-2-yl-, quinolin-2-yl-, quinolin-5-yl-, benzothiazol-6-yl-, 4-methyl-benzothiazol-2-yl-, thietan-3-yl-, 1-oxo-thietan-3-yl-, 1,1-dioxo-thietan-3-yl-, and 3-methyl-thietan-3-yl-, more preferably thietan-3-yl-, 1-oxo-thietan-3-yl-, 1,1-dioxo-thietan-3-yl- and 3-methyl-thietan-3-yl-.

Preferably $R^3$ is chlorodifluoromethyl or trifluoromethyl, most preferably trifluoro-methyl.

Preferably $R^4$ is aryl or aryl substituted by one to five $R^{10}$, more preferably aryl substituted by two to three $R^{10}$, more preferably phenyl substituted by two to three $R^{10}$, even more preferably 3,5-dibromo-phenyl-, 3,5-dichloro-phenyl-, 3,4-dichloro-phenyl-, 4-bromo-3,5-dichloro-phenyl or 3,4,5-trichloro-phenyl-, even more preferably 3,5-dibromo-phenyl-, 3,5-dichloro-phenyl-, 3,4-dichloro-phenyl-, or 3,4,5-trichloro-phenyl-, most preferably $R^4$ is 3,5-dichloro-phenyl.

Preferably each $R^5$ is independently hydrogen, halogen, cyano, nitro, $C_1$-$C_8$alkyl, $C_1$-$C_8$haloalkyl, $C_1$-$C_8$alkoxy, or $C_1$-$C_8$haloalkoxy, more preferably hydrogen, bromo, chloro, fluoro, cyano, nitro, methyl, ethyl, trifluoromethyl, methoxy, difluoromethoxy, or trifluoromethoxy, even more preferably hydrogen, bromo, chloro, fluoro, nitro, or methyl, more preferably hydrogen or methyl, most preferably hydrogen.

Preferably each $R^6$ is independently hydrogen, methyl or ethyl, more preferably hydrogen or methyl, most preferably hydrogen.

Preferably each $R^7$ is independently halogen, cyano, nitro, hydroxy, $C_1$-$C_8$alkoxy, $C_1$-$C_8$haloalkoxy, mercapto, $C_1$-$C_8$alkylthio-, $C_1$-$C_8$haloalkylthio-, more preferably bromo, chloro, fluoro, methyl, methoxy, or methylthio, preferably bromo, chloro, fluoro, methoxy, or methylthio, most preferably chloro, fluoro, or methoxy.

Preferably each $R^8$ is independently chloro, fluoro or methyl, most preferably methyl.

Preferably each $R^9$ is independently halogen, cyano, nitro, $C_1$-$C_8$alkyl, $C_1$-$C_8$haloalkyl, $C_1$-$C_8$alkoxy, $C_1$-$C_8$haloalkoxy, more preferably bromo, chloro, fluoro, cyano, nitro, methyl, ethyl, trifluoromethyl, methoxy, difluoromethoxy, or trifluoromethoxy, preferably bromo, chloro, fluoro, nitro, methoxy or methyl, preferably bromo, chloro, fluoro, nitro, or methyl, e.g. bromo, chloro, fluoro, methoxy or methyl.

Preferably each $R^{10}$ is independently halogen, $C_1$-$C_8$alkoxy, $C_1$-$C_8$haloalkoxy, $C_1$-$C_8$alkylthio-, or $C_1$-$C_8$haloalkylthio-, more preferably bromo, chloro, fluoro, methoxy, or methylthio, most preferably bromo or chloro.

Preferably each $R^{11}$ is independently bromo, chloro, fluoro, cyano, nitro, methyl, ethyl, trifluoromethyl, methoxy, difluoromethoxy, or trifluoromethoxy, more preferably bromo, chloro, fluoro, nitro, or methyl, most preferably chloro, fluoro, or methyl.

For example, the present invention provides compounds of formula (I) wherein $A^1$, $A^2$ and $A^3$ are independently C—$R^5$, nitrogen, N—$R^6$, oxygen or sulfur, provided that two of $A^1$, $A^2$ or $A^3$ are C—$R^5$ or nitrogen and that one of $A^1$, $A^2$ or $A^3$ is N—$R^6$, oxygen or sulfur;

$A^4$ and $A^5$ are independently C—$R^5$ or nitrogen;

$G^1$ is oxygen or sulfur;

$R^1$ is hydrogen, $C_1$-$C_8$alkyl, $C_1$-$C_8$alkylcarbonyl-, or $C_1$-$C_8$alkoxycarbonyl-;

$R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one to five $R^8$, aryl-$C_1$-$C_4$alkylene- or aryl-$C_1$-$C_4$alkylene- wherein the aryl moiety is substituted by one to five $R^9$, heterocyclyl-$C_1$-$C_4$alkylene- or heterocyclyl-$C_1$-$C_4$alkylene- wherein the heterocyclyl moiety is substituted by one to five $R^9$, aryl or aryl substituted by one to five $R^9$, or heterocyclyl or heterocyclyl substituted by one to five $R^9$;

$R^3$ is $C_1$-$C_8$haloalkyl;

$R^4$ is aryl or aryl substituted by one to five $R^{10}$, or heteroaryl or heteroaryl substituted by one to five $R^{10}$;

each $R^5$ is independently hydrogen, halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^6$ is independently hydrogen or $C_1$-$C_8$alkyl;

each $R^7$ is independently halogen, cyano, nitro, hydroxy, $C_1$-$C_8$alkoxy, $C_1$-$C_8$haloalkoxy, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^8$ is independently halogen or $C_1$-$C_8$alkyl;

each $R^9$ and $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{11}$, or heterocyclyl or heterocyclyl substituted by one to five $R^{11}$; and each $R^{11}$ is independently halogen, cyano, nitro, $C_1$-$C_4$alkyl, $C_1$-$C_4$haloalkyl, $C_1$-$C_4$alkoxy, or $C_1$-$C_4$haloalkoxy; or a salt or N-oxide thereof;

provided that -$A^1$-$A^2$-$A^3$- is not —O—($CR^5$)=N—, —S—($CR^5$)=N—, N=($CR^5$)—O— or —N=($CR^5$)—S— irrespective of the values for $A^4$ and $A^5$, and provided that -$A^1$-$A^2$-$A^3$- is not —($CR^5$)=($CR^5$)—O—, —O—($CR^5$)=($CR^5$)—, —($CR^5$)=($CR^5$)—S—, —S—($CR^5$)=($CR^5$)—, —($CR^5$)=($CR^5$)—($NR^6$)—, —($NR^6$)—($CR^5$)=($CR^5$)—, —($CR^5$)=N—($NR^6$)— and —($NR^6$)—N=($CR^5$)— when $A^4$ and $A^5$ are both C—$R^5$.

For example, the present invention provides compounds of formula (I) wherein $A^1$ and $A^3$ are nitrogen or N—$R^6$ and $A^2$ is C—$R^5$, N—$R^6$, nitrogen or sulfur, provided that two of $A^1$, $A^2$ or $A^3$ are C—$R^5$ or nitrogen and that one of $A^1$, $A^2$ or $A^3$ is N—$R^6$ or sulfur;

$A^4$ and $A^5$ are independently C—H or nitrogen;

$G^1$ is oxygen;

$R^1$ is hydrogen, methyl, ethyl, methylcarbonyl-, or methoxycarbonyl-;

$R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one to five $R^8$, aryl-$C_1$-$C_4$alkylene- or aryl-$C_1$-$C_4$alkylene- wherein the aryl moiety is substituted by one to five $R^9$, heterocyclyl-$C_1$-$C_4$alkylene- or heterocyclyl-$C_1$-$C_4$alkylene- wherein the heterocyclyl moiety is substituted by one to five $R^9$, aryl or aryl substituted by one to five $R^9$, heterocyclyl or heterocyclyl substituted by one to five $R^9$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from pyridyl, pyrazolyl, benzimidazolyl, furanyl, thiazolyl, oxetanyl, thietanyl, oxo-thietanyl and dioxo-thietanyl;

$R^3$ is $C_1$-$C_8$haloalkyl;

$R^4$ is phenyl substituted by two to three $R^{10}$;

$R^5$ is independently hydrogen, halogen, cyano, nitro, $C_1$-$C_8$alkyl, $C_1$-$C_8$haloalkyl, $C_1$-$C_8$alkoxy, or $C_1$-$C_8$haloalkoxy;

$R^6$ is hydrogen or $C_1$-$C_8$alkyl;

each $R^7$ is independently bromo, chloro, fluoro, methyl, methoxy, or methylthio;

each $R^8$ is independently chloro, fluoro or methyl;

each $R^9$ is independently halogen, cyano, nitro, $C_1$-$C_8$alkyl, $C_1$-$C_8$haloalkyl, $C_1$-$C_8$alkoxy or $C_1$-$C_8$haloalkoxy;

each $R^{10}$ is independently halogen, $C_1$-$C_8$alkoxy, $C_1$-$C_8$haloalkoxy, $C_1$-$C_8$alkylthio-, or $C_1$-$C_8$haloalkylthio-.

For example, the present invention provides compounds of formula (I) wherein $A^1$ and $A^3$ are nitrogen or N—$R^6$ and $A^2$ is C—$R^5$, N—$R^6$, nitrogen or sulfur, preferably $A^2$ is N—$R^6$, nitrogen or sulfur, and provided that two of $A^1$, $A^2$ or $A^3$ are C—$R^5$ or nitrogen and that one of $A^1$, $A^2$ or $A^3$ is N—$R^6$ or sulfur;

$A^4$ and $A^5$ are C—H;

$G^1$ is oxygen;

$R^1$ is hydrogen, methyl or ethyl;

$R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one to five $R^8$, phenyl-$C_1$-$C_4$alkylene- or phenyl-$C_1$-$C_4$alkylene-wherein the phenyl moiety is substituted by one to five $R^9$, pyridyl-$C_1$-$C_4$alkylene- or pyridyl-$C_1$-$C_4$alkylene- wherein the pyridyl moiety is substituted by one to four $R^9$, imidazolyl-$C_1$-$C_4$alkylene or imidazolyl- $C_1$-$C_4$alkylene wherein the imidazolyl moiety is substituted by one to five $R^9$, oxetanyl or oxetanyl substituted by one to five $R^9$, thietanyl or thietanyl substituted by one to five $R^9$, oxo-thietanyl or oxo-thietanyl substituted by one to five $R^9$, dioxo-thietanyl or dioxo-thietanyl substituted by one to five $R^9$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene;

$R^3$ is chlorodifluoromethyl or trifluoromethyl;

$R^4$ is 3,5-dibromo-phenyl-, 3,5-dichloro-phenyl-, 3,4-dichloro-phenyl-, 4-bromo-3,5-dichloro-phenyl or 3,4,5-trichloro-phenyl-;

$R^5$ is independently hydrogen, bromo, chloro, fluoro, cyano, nitro, methyl, ethyl, trifluoromethyl, methoxy, difluoromethoxy, or trifluoromethoxy;

$R^6$ is hydrogen, methyl or ethyl;

each $R^7$ is independently bromo, chloro, fluoro, methyl, methoxy, or methylthio;

each $R^8$ is methyl;

each $R^9$ is independently bromo, chloro, fluoro, cyano, nitro, methyl, ethyl, trifluoromethyl, methoxy, difluoromethoxy, or trifluoromethoxy.

For example, the present invention provides compounds of formula (I) wherein

-$A^1$-$A^2$-$A^3$- is selected from =N—S—N=, —N=C($R^5$)—N($R^6$)—, —N($R^6$)—C($R^5$)=N—, =N—N($R^6$)—N=, —N=N—N($R^6$)— and —N($R^6$)—N=N—, preferably N—S—N=N—N($R^6$)—N=, —N=N—N($R^6$)— and —N($R^6$)—N=N—;

$A^4$ and $A^5$ are C—H;

$G^1$ is oxygen;

$R^1$ is hydrogen;

$R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one or two methyl groups, phenyl-$C_1$-$C_4$alkylene- or phenyl-$C_1$-$C_4$alkylene- wherein the phenyl moiety is substituted by one to five $R^9$, pyridyl-$C_1$-$C_4$alkylene- or pyridyl-$C_1$-$C_4$alkylene- wherein the pyridyl moiety is substituted by one to four $R^9$, imidazolyl-$C_1$-$C_4$alkylene or imidazolyl-$C_1$-$C_4$alkylene wherein the imidazolyl moiety is substituted by one to five $R^9$, oxetanyl or oxetanyl substituted by one to five $R^9$, thietanyl or thietanyl substituted by one to five $R^9$, oxo-thietanyl or oxo-thietanyl substituted by one to five $R^9$, dioxo-thietanyl or dioxo-thietanyl substituted by one to five $R^9$;

$R^3$ is trifluoromethyl;

$R^4$ is 3,5-dichloro-phenyl;

$R^5$ is hydrogen or methyl;

$R^6$ is hydrogen or methyl;

each $R^7$ is independently bromo, chloro, fluoro, methoxy, or methylthio;

each $R^9$ is independently bromo, chloro, fluoro, nitro, or methyl.

For example, the present invention provides compounds of formula (I) wherein

-$A^1$-$A^2$-$A^3$- is selected from =N—S—N=, —N=C($R^5$)—N($R^6$)—, =N—N($R^6$)—N=, and —N=N—N($R^6$)—, preferably =N—S—N=, =N—N($R^6$)—N=, and —N=N—N($R^6$)—;

$A^4$ and $A^5$ are C—H;

$G^1$ is oxygen;

$R^1$ is hydrogen;

$R^2$ is $C_3$-$C_6$alkyl or $C_3$-$C_6$alkyl substituted by one to five $R^7$, $C_4$-$C_8$cycloalkyl or $C_4$-$C_8$cycloalkyl substituted by one or two methyl groups, phenyl-$C_1$-$C_2$alkylene- or phenyl-$C_1$-$C_2$alkylene- wherein the phenyl moiety is substituted by one to five $R^9$, pyridyl-$C_1$-$C_2$alkylene- or pyridyl-$C_1$-$C_2$alkylene- wherein the pyridyl moiety is substituted by one to four $R^9$, imidazolyl-$C_1$-$C_2$alkylene- or imidazolyl-$C_1$-$C_2$alkylene- wherein the imidazolyl moiety is substituted by one to five $R^9$, oxetanyl or oxetanyl substituted by one to five $R^9$, thietanyl or thietanyl substituted by one to five $R^9$, oxo-thietanyl or oxo-thietanyl substituted by one to five $R^9$, dioxo-thietanyl or dioxo-thietanyl substituted by one to five $R^9$;

$R^3$ is trifluoromethyl;

$R^4$ is 3,5-dichloro-phenyl;

$R^5$ is hydrogen or methyl;

$R^6$ is hydrogen or methyl;

each $R^7$ is independently bromo, chloro, fluoro, methoxy, or methylthio;

each $R^9$ is independently bromo, chloro, fluoro, methoxy or methyl.

For example, the present invention provides compounds of formula (I) wherein

-$A^1$-$A^2$-$A^3$- is =N—S—N=;

$A^4$ and $A^5$ are CH;

$G^1$ is oxygen;

$R^1$ is hydrogen;

$R^2$ is $C_3$-$C_6$alkyl or $C_3$-$C_6$alkyl substituted by one to three $R^7$, $C_4$-$C_8$cycloalkyl, phenyl-methylene- or phenyl-methylene- wherein the phenyl moiety is substituted by one to three $R^9$, imidazolyl-methylene- or imidazolyl-methylene- wherein the imidazolyl moiety is substituted by one to three $R^9$, thietanyl or methylthietanyl, oxo-thietanyl or methyl-oxo-thietanyl, dioxo-thietanyl or methyl-dioxo-thietanyl;

$R^3$ is trifluoromethyl;

$R^4$ is 3,5-dichloro-phenyl;

$R^6$ is hydrogen or methyl;

each $R^7$ is independently bromo, chloro, fluoro, methoxy, or methylthio;

each $R^9$ is independently bromo, chloro, fluoro, methoxy or methyl.

A preferred embodiment are compounds of formula (IA) wherein $A^1$ is N, $A^2$ is S and $A^3$ is N, $A^4$ is C—H, $A^5$ is C—H, and $G^1$, $R^1$, $R^2$, $R^3$, $R^4$, $R^6$, $R^7$, $R^8$, and $R^9$ are as defined for a compound of formula (I); or a salt or N-oxide thereof.

A preferred embodiment are compounds of formula (IB) wherein $A^1$ is N, $A^2$ is C—H and $A^3$ is N—H, $A^4$ is C—H, $A^5$ is C—H, and $G^1$, $R^1$, $R^2$, $R^3$, $R^4$, $R^6$, $R^7$, $R^8$, and $R^9$ are as defined for a compound of formula (I); or a salt or N-oxide thereof.

A preferred embodiment are compounds of formula (IC) wherein $A^1$ is N, $A^2$ is C—H and $A^3$ is N-Me, $A^4$ is C—H, $A^5$ is C—H, and $G^1$, $R^1$, $R^2$, $R^3$, $R^4$, $R^6$, $R^7$, $R^8$, and $R^9$ are as defined for a compound of formula (I); or a salt or N-oxide thereof.

A preferred embodiment are compounds of formula (ID) wherein $A^1$ is N, $A^2$ is N and $A^3$ is N—H, $A^4$ is C—H, $A^5$ is C—H, and $G^1$, $R^1$, $R^2$, $R^3$, $R^4$, $R^6$, $R^7$, $R^8$, and $R^9$ are as defined for a compound of formula (I); or a salt or N-oxide thereof.

A preferred embodiment are compounds of formula (IE) wherein $A^1$ is N, $A^2$ is N and $A^3$ is N-Me, $A^4$ is C—H, $A^5$ is C—H, and $G^1$, $R^1$, $R^2$, $R^3$, $R^4$, $R^6$, $R^7$, $R^8$, and $R^9$ are as defined for a compound of formula (I); or a salt or N-oxide thereof.

Certain intermediates are novel and as such form a further aspect of the invention. One group of novel intermediates are compounds of formula (II)

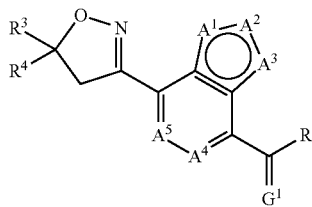

(II)

wherein $A^1, A^2, A^3, A^4, A^5, G^1, R^3$ and $R^4$ are as defined for a compound of formula (I), and R is hydroxy, $C_1$-$C_6$alkoxy or halogen, such as bromo, chloro or fluoro; or a salt or N-oxide thereof. The preferences for $A^1, A^2, A^3, A^4, A^5, G^1, R^3$ and $R^4$ are the same as the preferences set out for the corresponding substituents of a compound of formula (I). Preferably R is hydroxy, $C_1$-$C_6$alkoxy or chloro.

A further group of novel intermediates are compounds of formula (IV)

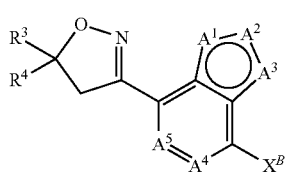

(IV)

wherein $A^1, A^2, A^3, A^4, A^5, R^3$ and $R^4$ are as defined for a compound of formula (I), and $X^B$ is halogen, such as bromo, chloro or fluoro; or a salt or N-oxide thereof. The preferences for $A^1, A^2, A^3, A^4, A^5, R^3$ and $R^4$ are the same as the preferences set out for the corresponding substituents of a compound of formula (I). Preferably $X^B$ is bromo.

A further group of novel intermediates are compounds of formula (XI)

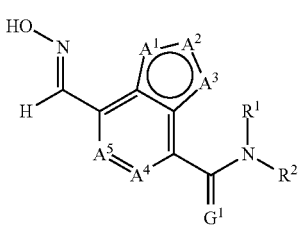

(XI)

wherein $A^1, A^2, A^3, A^4, A^5, G^1, R^1$ and $R^2$ are as defined for a compound of formula (I); or a salt or N-oxide thereof. The preferences for $A^1, A^2, A^3, A^4, A^5, G^1, R^1$ and $R^2$ are the same as the preferences set out for the corresponding substituents of a compound of formula (I).

A further group of novel intermediates are compounds of formula (XII)

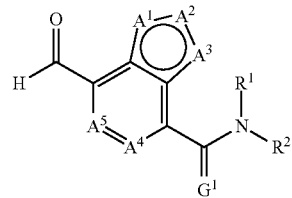

(XII)

wherein $A^1, A^2, A^3, A^4, A^5, G^1, R^1$ and $R^2$ are as defined for a compound of formula (I); or a salt or N-oxide thereof. The preferences for $A^1, A^2, A^3, A^4, A^5, G^1, R^1$ and $R^2$ are the same as the preferences set out for the corresponding substituents of a compound of formula (I).

A further group of novel intermediates are compounds of formula (XIV)

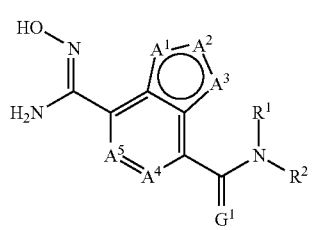

(XIV)

wherein $A^1, A^2, A^3, A^4, A^5, G^1, R^1$ and $R^2$ are as defined for a compound of formula (I); or a salt or N-oxide thereof. The preferences for $A^1, A^2, A^3, A^4, A^5, G^1, R^1$ and $R^2$ are the same as the preferences set out for the corresponding substituents of a compound of formula (I).

A further group of novel intermediates are compounds of formula (XV)

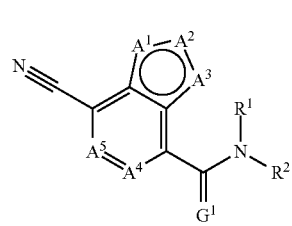

(XV)

wherein $A^1, A^2, A^3, A^4, A^5, G^1, R^1$ and $R^2$ are as defined for a compound of formula (I); or a salt or N-oxide thereof. The preferences for $A^1, A^2, A^3, A^4, A^5, G^1, R^1$ and $R^2$ are the same as the preferences set out for the corresponding substituents of a compound of formula (I).

A further group of novel intermediates are compounds of formula (XVIII)

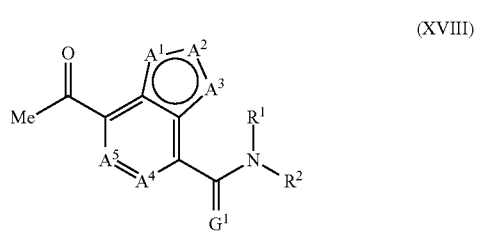

(XVIII)

wherein $A^1, A^2, A^3, A^4, A^5, G^1, R^1$ and $R^2$ are as defined for a compound of formula (I); or a salt or N-oxide thereof. The preferences for $A^1, A^2, A^3, A^4, A^5, G^1, R^1$ and $R^2$ are the same as the preferences set out for the corresponding substituents of a compound of formula (I).

A further group of novel intermediates are compounds of formula (XIX)

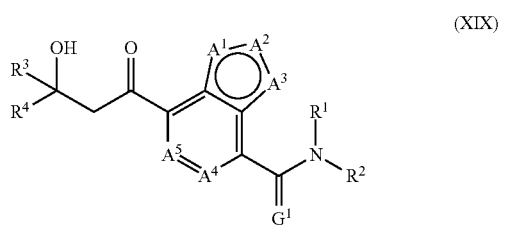

(XIX)

wherein $A^1, A^2, A^3, A^4, A^5, G^1, R^1, R^2, R^3$ and $R^4$ are as defined for a compound of formula (I); or a salt or N-oxide thereof. The preferences for $A^1, A^2, A^3, A^4, A^5, G^1, R^1, R^2, R^3$ and $R^4$ are the same as the preferences set out for the corresponding substituents of a compound of formula (I).

A further group of novel intermediates are compounds of formula (XX)

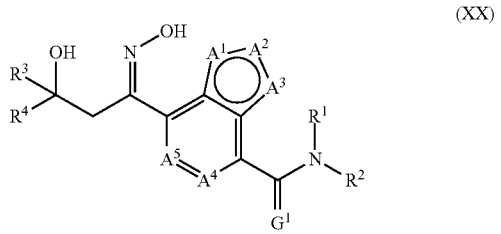

(XX)

wherein $A^1, A^2, A^3, A^4, A^5, G^1, R^1, R^2, R^3$ and $R^4$ are as defined for a compound of formula (I); or a salt or N-oxide thereof. The preferences for $A^1, A^2, A^3, A^4, A^5, G^1, R^1, R^2, R^3$ and $R^4$ are the same as the preferences set out for the corresponding substituents of a compound of formula (I).

A further group of novel intermediates are compounds of formula (XXII)

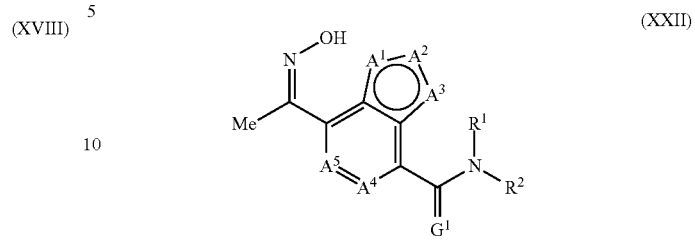

(XXII)

wherein $A^1, A^2, A^3, A^4, A^5, G^1, R^1$ and $R^2$ are as defined for a compound of formula (I); or a salt or N-oxide thereof. The preferences for $A^1, A^2, A^3, A^4, A^5, G^1, R^1$ and $R^2$ are the same as the preferences set out for the corresponding substituents of a compound of formula (I).

A further group of novel intermediates are compounds of formula (XXIII)

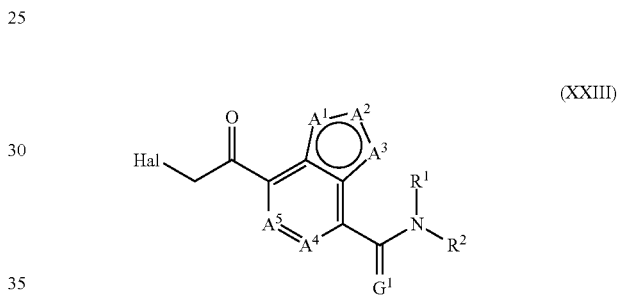

(XXIII)

wherein $A^1, A^2, A^3, A^4, A^5, G^1, R^1$ and $R^2$ are as defined for a compound of formula (I), and Hal is a halogen, such as such as bromo or chloro; or a salt or N-oxide thereof. The preferences for $A^1, A^2, A^3, A^4, A^5, G^1, R^1$ and $R^2$ are the same as the preferences set out for the corresponding substituents of a compound of formula (I).

A further group of novel intermediates are compounds of formula (XXIV)

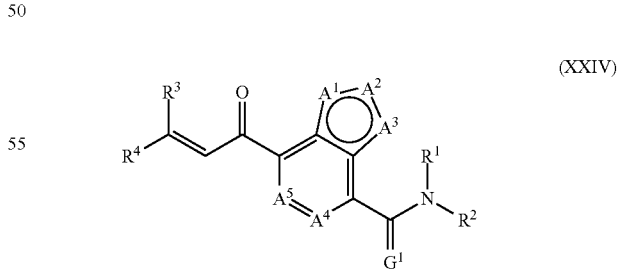

(XXIV)

wherein $A^1, A^2, A^3, A^4, A^5, G^1, R^1, R^2, R^3$ and $R^4$ are as defined for a compound of formula (I); or a salt or N-oxide thereof. The preferences for $A^1, A^2, A^3, A^4, A^5, G^1, R^1, R^2, R^3$ and $R^4$ are the same as the preferences set out for the corresponding substituents of a compound of formula (I).

In a further aspect, the present invention provides a compound of formula (A)

(A)

wherein
$A^1$, $A^2$ and $A^3$ are independently C—$R^5$, nitrogen, N—$R^6$, oxygen or sulfur, provided that two of $A^1$, $A^2$ or $A^3$ are C—$R^5$ or nitrogen and that one of $A^1$, $A^2$ or $A^3$ is N—$R^6$, oxygen or sulfur;
$A^4$ and $A^5$ are independently C—$R^5$ or nitrogen;
$G^1$ is oxygen or sulfur;
$R^1$ is hydrogen, $C_1$-$C_8$alkyl, $C_1$-$C_8$alkylcarbonyl-, or $C_1$-$C_8$alkoxycarbonyl-;
$R^2$ is cyclobutyl or cyclobutyl substituted by one to five $R^8$, oxetanyl or oxetanyl substituted by one to five $R^9$, thietanyl or thietanyl substituted by one to five $R^9$, oxo-thietanyl or oxo-thietanyl substituted by one to five $R^9$, or dioxo-thietanyl or dioxo-thietanyl substituted by one to five $R^9$;
$R^3$ is $C_1$-$C_8$haloalkyl;
$R^4$ is aryl or aryl substituted by one to five $R^{10}$, or heteroaryl or heteroaryl substituted by one to five $R^{10}$;
each $R^5$ is independently hydrogen, halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^6$ is independently hydrogen or $C_1$-$C_8$alkyl;
each $R^8$ is independently halogen or $C_1$-$C_8$alkyl;
each $R^9$ and $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{11}$, or heterocyclyl or heterocyclyl substituted by one to five $R^{11}$; and
each $R^{11}$ is independently halogen, cyano, nitro, $C_1$-$C_4$alkyl, $C_1$-$C_4$haloalkyl, $C_1$-$C_4$alkoxy, or $C_1$-$C_4$haloalkoxy; or a salt or N-oxide thereof;
Preferably $A^1$ is nitrogen, C—$R^5$ or N—$R^6$, most preferably nitrogen or N—$CH_3$.
Preferably $A^2$ is C—$R^5$, nitrogen or sulfur.
Preferably $A^3$ is nitrogen C—$R^5$ or N—$R^6$, most preferably nitrogen or N—$CH_3$.
Preferably -$A^1$-$A^2$-$A^3$- is selected from =N—S—N=, —S—N=N—, —N=N—S—, =N—N($R^6$)—N=, —N=N—N($R^6$)—, —N($R^6$)—N=N—, —C($R^5$)=N—N($R^6$)—, —N($R^6$)—N=C($R^5$)—, —N=C($R^5$)—N($R^6$)—, —N($R^6$)—C($R^5$)=N—, —N=C($R^5$)—O—, —O—C($R^5$)=N—, =N—O—C($R^5$)= and =C($R^5$)—O—N=, more preferably -$A^1$-$A^2$-$A^3$- is selected from =N—S—N=, —S—N=N—, —N=N—S—, =N—N($R^6$)—N=, —N=N—N($R^6$)—, —N($R^6$)—N=N—, —C($R^5$)=N—N ($R^6$)—, —N($R^6$)—N=C($R^5$)—, —N=C($R^5$)—N($R^6$)—, —N($R^6$)—C($R^5$)=N—, —N=C($R^5$)—O— and —O—C ($R^5$)=N—, more preferably =N—S—N=, —N=C($R^5$)—N($R^6$)—, —N=N—N($R^6$)—, =N—N($R^6$)—N=, —C($R^5$)=N—N($R^6$)— and —N=C($R^5$)—O—, more preferably =N—S—N=, —N=C($R^5$)—N($R^6$)—, —N=N—N ($R^6$)—, =N—N($R^6$)—N= and —C($R^5$)=N—N($R^6$)—, more preferably =N—S—N=, —N=N—N($R^6$)— and =N—N($R^6$)—N=, most preferably =N—S—N=.
$R^2$ is preferably cyclobutyl or cyclobutyl substituted by one to five $R^8$, thietanyl or thietanyl substituted by one to five $R^9$, oxo-thietanyl or oxo-thietanyl substituted by one to five $R^9$, or dioxo-thietanyl or dioxo-thietanyl substituted by one to five $R^9$, more preferably thietanyl or methylthietanyl, oxo-thietanyl or methyl-oxothietanyl, dioxo-thietanyl or methyl-dioxo-thietanyl, more preferably thietanyl, oxo-thietanyl or dioxo-thietanyl.
The preferred definitions for $A^4$, $A^5$, $G^1$, $R^1$, $R^3$, $R^4$, $R^5$, $R^6$, $R^8$, $R^9$, $R^{10}$ and $R^{11}$ are as described for compounds of formula (A).
For example, the present invention provides compounds of formula (A) wherein
-$A^1$-$A^2$-$A^3$- is selected from =N—S—N=, —S—N=N—, —N=N—S—, =N—N($R^6$)—N=, —N=N—N($R^6$)—, —N($R^6$)—N=N—, —C($R^5$)=N—N ($R^6$)—, —N($R^6$)—N=C($R^5$)—, —N=C($R^5$)—N($R^6$)—, —N($R^6$)—C($R^5$)=N—, —N=C($R^5$)—O— and —O—C ($R^5$)=N—;
$A^4$ and $A^5$ are independently C—H or nitrogen;
$G^1$ is oxygen;
$R^1$ is hydrogen, methyl, ethyl, methylcarbonyl-, or methoxycarbonyl-;
$R^2$ is cyclobutyl or cyclobutyl substituted by one to five $R^8$, oxetanyl or oxetanyl substituted by one to five $R^9$, thietanyl or thietanyl substituted by one to five $R^9$, oxo-thietanyl or oxo-thietanyl substituted by one to five $R^9$, or dioxo-thietanyl or dioxo-thietanyl substituted by one to five $R^9$;
$R^3$ is $C_1$-$C_8$haloalkyl;
$R^4$ is phenyl substituted by two to three $R^{10}$;
$R^5$ is hydrogen, bromo, chloro, fluoro, cyano, nitro, methyl, ethyl, trifluoromethyl, methoxy, difluoromethoxy, or trifluoromethoxy;
$R^6$ is hydrogen or $C_1$-$C_8$alkyl;
each $R^8$ is independently chloro, fluoro or methyl;
each $R^9$ is independently halogen, cyano, nitro, $C_1$-$C_8$alkyl, $C_1$-$C_8$haloalkyl, $C_1$-$C_8$alkoxy, $C_1$-$C_8$haloalkoxy;
each $R^{10}$ is independently halogen, $C_1$-$C_8$alkoxy, $C_1$-$C_8$haloalkoxy, $C_1$-$C_8$alkylthio-, or $C_1$-$C_8$haloalkylthio-.
For example, the present invention provides compounds of formula (A) wherein
-$A^1$-$A^2$-$A^3$- is selected from =N—S—N=, —N=C ($R^5$)—N($R^6$)—, —N=N—N($R^6$)—, =N—N($R^6$)—N=, —C($R^5$)=N—N($R^6$)— and —N=C($R^5$)—O—;
$A^4$ and $A^5$ are C—H;
$G^1$ is oxygen;
$R^1$ is hydrogen, methyl or ethyl;
$R^2$ is cyclobutyl or cyclobutyl substituted by one to five $R^8$, oxetanyl or oxetanyl substituted by one to five $R^9$, thietanyl or thietanyl substituted by one to five $R^9$, oxo-thietanyl or oxo-thietanyl substituted by one to five $R^9$, or dioxo-thietanyl or dioxo-thietanyl substituted by one to five $R^9$;
$R^3$ is chlorodifluoromethyl or trifluoromethyl;
$R^4$ is 3,5-dibromo-phenyl-, 3,5-dichloro-phenyl-, 3,4-dichloro-phenyl- or 3,4,5-trichloro-phenyl-, most preferably $R^4$ is 3,5-dichloro-phenyl;
$R^5$ is hydrogen, bromo, chloro, fluoro, nitro, or methyl
$R^6$ is hydrogen, methyl or ethyl;
each $R^8$ is methyl;

each $R^9$ is independently bromo, chloro, fluoro, cyano, nitro, methyl, ethyl, trifluoromethyl, methoxy, difluoromethoxy, or trifluoromethoxy.

For example, the present invention provides compounds of formula (A) wherein $-A^1-A^2-A^3-$ is selected from $=N-S-N=$, $-N=C(R^5)-N(R^6)-$, $-N=N-N(R^6)-$, $=N-N(R^6)-N=$ and $-C(R^5)=N-N(R^6)-$;

$A^4$ and $A^5$ are C—H;

$G^1$ is oxygen;

$R^1$ is hydrogen;

$R^2$ is cyclobutyl, thietanyl or methylthietanyl, oxo-thietanyl or methyl-oxo-thietanyl, or dioxo-thietanyl or methyl-dioxo-thietanyl;

$R^3$ is trifluoromethyl;

$R^4$ is 3,5-dichloro-phenyl;

$R^5$ is hydrogen or methyl;

$R^6$ is hydrogen or methyl.

Any reference herein to uses and/or compositions of compounds of formula (I) also applies equally to compounds of formula (A).

The compounds in Tables 1 to 5 below illustrate the compounds of the invention.

TABLE 1

Table 1 provides 51 compounds of formula (Ia) wherein $G^1$ is oxygen, $R^3$ is trifluoromethyl, $R^4$ is 3,5-dichloro-phenyl-, and $R^1$ and $R^2$ have the values listed in the table below.

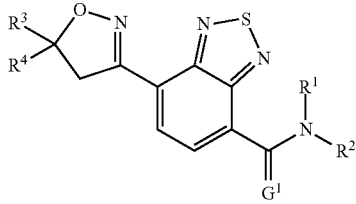

(Ia)

| Compound numbers | $R^1$ | $R^2$ |
|---|---|---|
| 1.01 | H | ethyl- |
| 1.02 | H | butyl- |
| 1.03 | H | but-2-yl- |
| 1.04 | H | 3-bromo-propyl- |
| 1.05 | H | 2,2,2-trifluoro-ethyl- |
| 1.06 | H | 3,3,3-trifluoro-propyl- |
| 1.07 | H | 2-methoxy-ethyl- |
| 1.08 | H | 1-methoxy-prop-2-yl- |
| 1.09 | H | cyclobutyl- |
| 1.10 | H | 2-methyl-cyclohex-1-yl- |
| 1.11 | H | phenyl-methyl- |
| 1.12 | H | 1-phenyl-eth-1-yl- |
| 1.13 | H | 2-phenyl-eth-1-yl- |
| 1.14 | H | (3-chloro-phenyl)-methyl- |
| 1.15 | H | (2-fluoro-phenyl)-methyl- |
| 1.16 | H | (4-methoxy-phenyl)-methyl- |
| 1.17 | H | (2-trifluoromethyl-phenyl)-methyl- |
| 1.18 | H | (2-trifluoromethoxy-phenyl)-methyl- |
| 1.19 | H | (pyrid-2-yl)-methyl- |
| 1.20 | H | (pyrid-3-yl)-methyl- |
| 1.21 | H | (2-chloro-pyrid-5-yl)-methyl- |
| 1.22 | H | (1-methyl-1H-imidazol-4-yl)-methyl- |
| 1.23 | H | (furan-2-yl)-methyl- |
| 1.24 | H | 2-(thiophen-2'-yl)-eth-1-yl- |
| 1.25 | H | 2-(indol-3'-yl)-eth-1-yl- |
| 1.26 | H | (1H-benzimidazol-2-yl)-methyl- |
| 1.27 | H | (oxetan-2-yl)-methyl- |
| 1.28 | H | (tetrahydrofuran-2-yl)-methyl- |
| 1.29 | H | 2-([1',3']dioxolan-2'-yl)-eth-1-yl- |
| 1.30 | H | 2-(morpholin-4'-yl)-eth-1-yl- |
| 1.31 | H | 2-(benzo[1',3']dioxol-5'-yl)-eth-1-yl- |

TABLE 1-continued

Table 1 provides 51 compounds of formula (Ia) wherein $G^1$ is oxygen, $R^3$ is trifluoromethyl, $R^4$ is 3,5-dichloro-phenyl-, and $R^1$ and $R^2$ have the values listed in the table below.

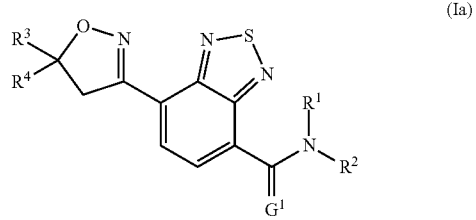

(Ia)

| Compound numbers | $R^1$ | $R^2$ |
|---|---|---|
| 1.32 | H | (2,3-dihydro-benzo[1,4]dioxin-6-yl)-methyl- |
| 1.33 | H | 2-chloro-phenyl- |
| 1.34 | H | 3-fluoro-phenyl- |
| 1.35 | H | 2-methyl-phenyl- |
| 1.36 | H | 2-chloro-6-methyl-phenyl- |
| 1.37 | H | 2-trifluoromethyl-phenyl- |
| 1.38 | H | 2,4-dimethoxy-phenyl- |
| 1.39 | H | 3-methyl-pyrid-2-yl- |
| 1.40 | H | 1,3-dimethyl-1H-pyrazol-5-yl- |
| 1.41 | H | 4-methyl-thiazol-2-yl- |
| 1.42 | H | 5-methyl-thiadiazol-2-yl- |
| 1.43 | H | quinolin-2-yl- |
| 1.44 | H | quinolin-5-yl- |
| 1.45 | H | benzothiazol-6-yl- |
| 1.46 | H | 4-methyl-benzothiazol-2-yl- |
| 1.47 | H | thietan-3-yl- |
| 1.48 | H | 1-oxo-thietan-3-yl- |
| 1.49 | H | 1,1-dioxo-thietan-3-yl- |
| 1.50 | H | 3-methyl-thietan-3-yl- |
| 1.51 | H | N-(2,2,2-Trifluoro-ethyl)-acetamide-2-yl |

TABLE 2

Table 2 provides 51 compounds of formula (Ib) wherein $G^1$ is oxygen, $R^3$ is trifluoromethyl, $R^4$ is 3,5-dichloro-phenyl-, and $R^1$ and $R^2$ have the values listed in Table 1 above.

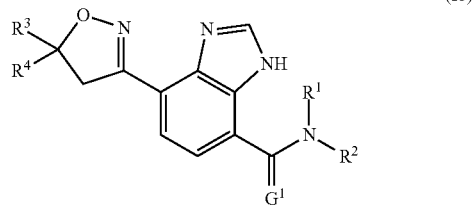

(Ib)

TABLE 3

Table 3 provides 51 compounds of formula (Ic) wherein $G^1$ is oxygen, $R^3$ is trifluoromethyl, $R^4$ is 3,5-dichloro-phenyl-, and $R^1$ and $R^2$ have the values listed in Table 1 above.

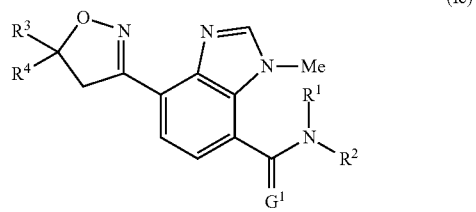

(Ic)

TABLE 4

Table 4 provides 51 compounds of formula (Id) wherein $G^1$ is oxygen, $R^3$ is trifluoromethyl, $R^4$ is 3,5-dichloro-phenyl-, and $R^1$ and $R^2$ have the values listed in Table 1 above.

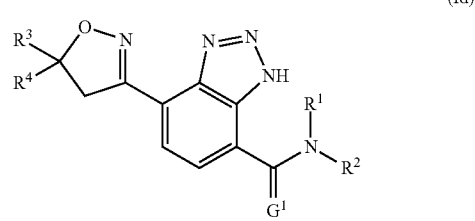

(Id)

TABLE 5

Table 5 provides 51 compounds of formula (Ie) wherein $G^1$ is oxygen, $R^3$ is trifluoromethyl, $R^4$ is 3,5-dichloro-phenyl-, and $R^1$ and $R^2$ have the values listed in Table 1 above.

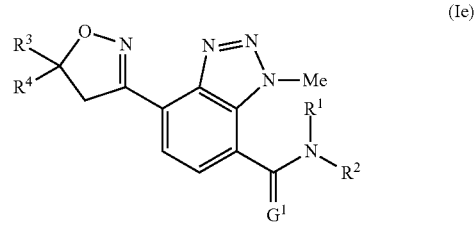

(Ie)

TABLE 6

Table 6 provides 51 compounds of formula (If) wherein $G^1$ is oxygen, $R^3$ is trifluoromethyl, $R^4$ is 3,5-dichloro-phenyl-, and $R^1$ and $R^2$ have the values listed in Table 1 above.

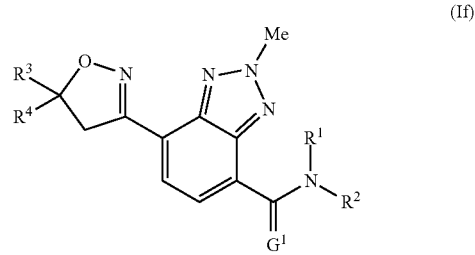

(If)

TABLE 7

Table 7 provides 5 compounds of formula (Ig) wherein $G^1$ is oxygen, $R^3$ is trifluoromethyl, $R^4$ is 3,5-dichloro-phenyl-, and $R^1$ and $R^2$ have the values listed below.

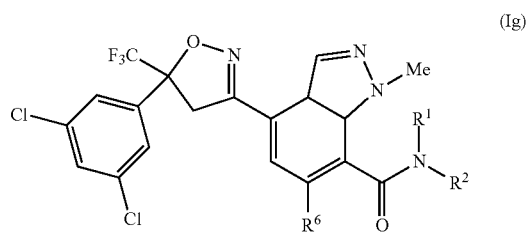

(Ig)

| Compound numbers | $R^1$ | $R^2$ |
|---|---|---|
| 7.01 | H | cyclobutyl- |
| 7.02 | H | thietan-3-yl- |
| 7.03 | H | 1-oxo-thietan-3-yl- |

TABLE 7-continued

| 7.04 | H | 1,1-dioxo-thietan-3-yl- |
| 7.05 | H | 3-methyl-thietan-3-yl- |

TABLE 8

Table 7 provides 5 compounds of formula (Ih) wherein $G^1$ is oxygen, $R^3$ is trifluoromethyl, $R^4$ is 3,5-dichloro-phenyl-, and $R^1$ and $R^2$ have the values listed in Table 7 above.

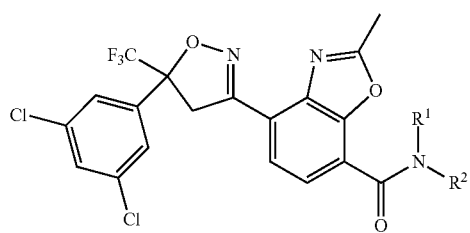

Ih

The compounds of the invention may be made by a variety of methods as shown in Schemes 1 to 8.

Scheme 1

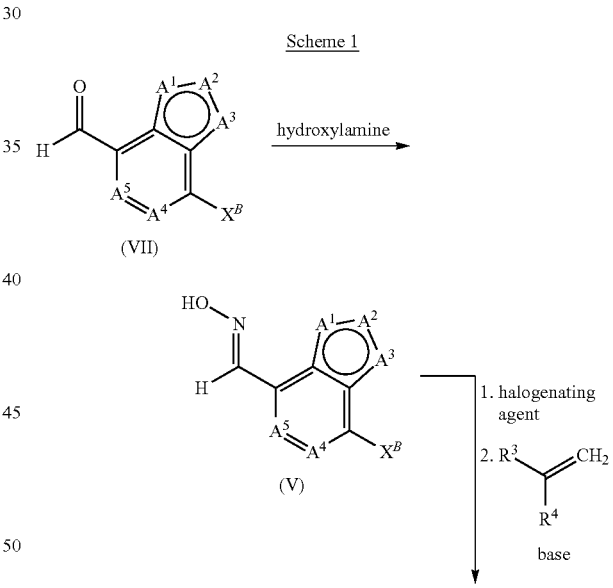

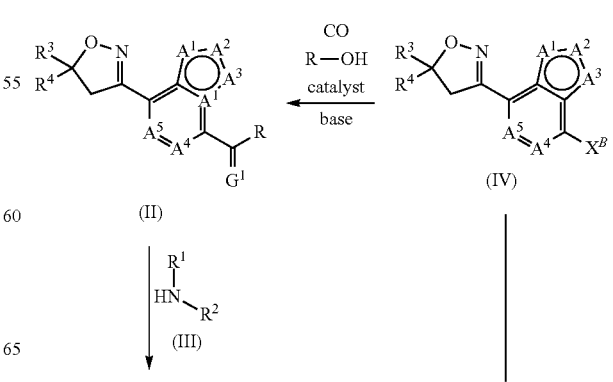

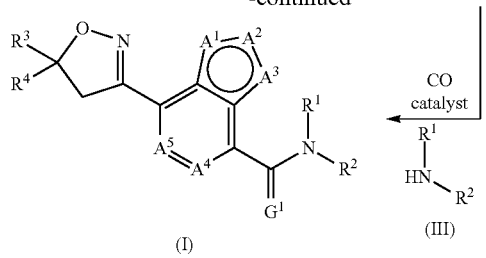

1) Compounds of formula (I) wherein $G^1$ is oxygen, can be prepared by reacting a compound of formula (II) wherein $G^1$ is oxygen and R is OH, $C_1$-$C_6$alkoxy or Cl, F or Br, with an amine of formula (III) as shown in Scheme 1. When R is OH such reactions are usually carried out in the presence of a coupling reagent, such as N,N'-dicyclohexylcarbo-diimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (III) are either commercially available or known in the literature, or can be prepared using methods known to a person skilled in the art.

2) Acid halides of formula (II), wherein $G^1$ is oxygen and R is Cl, F or Br, may be made from carboxylic acids of formula (II), wherein $G^1$ is oxygen and R is OH, under standard conditions, such as treatment with thionyl chloride or oxalyl chloride. A preferred solvent is dichloromethane. The reaction is carried out at a temperature of from 0° C. to 100° C., preferably from 15° C. to 30° C., in particular at ambient temperature.

3) Carboxylic acids of formula (II), wherein $G^1$ is oxygen and R is OH, may be formed from esters of formula (II), wherein $G^1$ is oxygen and R is $C_1$-$C_6$alkoxy. It is known to a person skilled in the art that there are many methods for the hydrolysis of such esters depending on the nature of the alkoxy group. One widely used method to achieve such a transformation is the treatment of the ester with an alkali hydroxide, such as lithium hydroxide, sodium hydroxide or potassium hydroxide, in a solvent, such as ethanol or tetrahydrofuran, in the presence of water. Another is the treatment of the ester with an acid, such as trifluoroacetic acid, in a solvent, such as dichloromethane, followed by addition of water. The reaction is carried out at a temperature of from 0° C. to 150° C., preferably from 15° C. to 100° C., in particular at 50° C.

4) Compounds of formula (II) wherein $G^1$ is oxygen and R is $C_1$-$C_6$alkoxy, can be prepared by reacting a compound of formula (IV) wherein $X^B$ is a leaving group, for example a halogen, such as bromo, with carbon monoxide and an alcohol of formula R—OH, such as ethanol, in the presence of a catalyst, such as bis(triphenylphosphine)palladium(II) dichloride, and in the presence of a base, such as pyridine, triethylamine, 4-(dimethylamino)-pyridine ("DMAP") or diisopropylethylamine (Hunig's base). The reaction is carried out at a temperature of from 50° C. to 200° C., preferably from 100° C. to 150° C., in particular at 115° C. The reaction is carried out at a pressure of from 50 to 200 bar, preferably from 100 to 150 bar, in particular at 120 bar.

5) Alternatively, compounds of formula (I) wherein $G^1$ is oxygen, can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis(triphenylphosphine)palladium(II)dichloride, in the presence of a base, such as sodium carbonate, pyridine, triethylamine, 4-(dimethyl-amino)-pyridine ("DMAP") or diisopropylethylamine (Hunig's base), optionally in the presence of a ligand, such as triphenylphosphine, in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

6) Compounds of formula (IV) wherein $X^B$ is a leaving group, for example a halogen, such as bromo, can be made by reaction of an oxime of formula (V) wherein $X^B$ is a leaving group, for example a halogen, such as bromo, and a vinyl compound of formula (VI) in a two step reaction. In the first step, the oxime of formula (V) is reacted with a halogenating agent, for example a succinimide, such as N-chlorosuccinimide ("NCS"), in the presence of a suitable solvent, for example a polar solvent, such as N,N-dimethylformamide. The first step is carried out at a temperature of from 0° C. to 100° C., preferably from 15° C. to 30° C., in particular at ambient temperature.

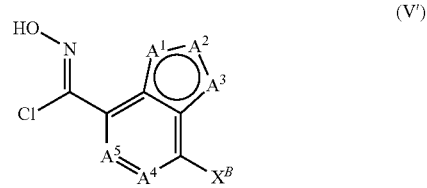

In the second step, the chloro hydroxy imine intermediate of formula (V') is reacted with the vinyl compound of formula (VI) in the presence of a base, for example an organic base, such as triethylamine, or an inorganic base, such as sodium hydrogen carbonate, in the presence of a suitable solvent, for example a polar solvent, such as N,N-dimethylformamide or isopropanol. It is possible to conduct these two steps separately and optionally to isolate the chloro hydroxy imine intermediate or more conveniently to conduct these two steps successively in one reaction vessel without isolation of the intermediate. The second step is carried out at a temperature of from 0° C. to 100° C., preferably from 15° C. to 30° C., in particular at ambient temperature. Vinyl compounds of formula (VI) are commercially available or can be made by methods known to a person skilled in the art.

7) Compounds of formula (V) wherein $X^B$ is a leaving group, for example a halogen, such as bromo, can be made by reaction of an aldehyde of formula (VII) wherein $X^B$ is a leaving group, for example a halogen, such as bromo, with a hydroxylamine, such as hydroxylamine hydrochloride. Such reactions are carried out optionally in the presence of a base, for example an organic base, such as triethylamine or sodium acetate, or an inorganic base, such as sodium hydrogen carbonate, optionally in the presence of a solvent, such as methanol, ethanol or water, or a mixture thereof. The reaction is carried out at a temperature of from 0° C. to 100° C., preferably from 15° C. to 30° C., in particular at ambient temperature. Aldehydes of formula (VII) are commercially available or can be made by methods known to a person skilled in the art.

8) Compounds of formula (I), wherein $G^1$ is sulfur, may be made by treatment of a compound of formula (II), wherein $G^1$ is oxygen and R is OH, $C_1$-$C_6$alkoxy or Cl, F or Br, with a thio-transfer reagent, such as Lawesson's reagent or phosphorus pentasulfide, prior to elaborating to compounds of formula (I), as described under 1).

9) Compounds of formula (I) with a sulfoxide group or a sulfone group can be made from a compound of formula (I) with a sulfide group (or sulfoxide group) in the corresponding position, by treatment with an oxidising reagent, such as potassium permanganate, 3-chloroperoxybenzoic acid ("MCPBA"), sodium periodate (optionally in the presence of ruthenium(II) oxide), hydrogen peroxide, oxone and sodium hypochlorite. One equivalent of oxidising reagent is required to convert a sulfide to a sulfoxide, or a sulfoxide to a sulfone. Two equivalents of oxidising reagent are required to convert a sulfide to a sulfone. Preferred solvents are tetrahydrofuran, dioxane, 1,2-dimethoxyethane, ethyl acetate, toluene, dichloromethane and water, or mixtures thereof. The reaction is optionally carried out in the presence of a base, for example a carbonate, such as sodium hydrogen carbonate. The reaction is carried out at a temperature of from 0° C. to 100° C., preferably from 15° C. to 30° C., in particular at ambient temperature.

10) Alternatively, compounds of formula (II) wherein $G^1$ is oxygen and R is $C_1$-$C_6$alkoxy, such as methoxy or tert-butoxy, can be prepared by reaction of an oxime of formula (VIII) wherein $G^1$ is oxygen and R is $C_1$-$C_6$alkoxy, such as methoxy or tert-butoxy, with a halogenating agent followed by a vinyl compound of formula (VI) and base as shown in Scheme 2 in a two step reaction as described under 6). The intermediate of formula (VIII'), wherein $G^1$ is oxygen and R is $C_1$-$C_6$alkoxy, such as methoxy or tert-butoxy, can optionally be isolated.

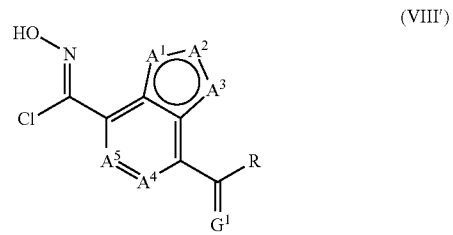

(VIII')

11) Compounds of formula (VIII) wherein $G^1$ is oxygen and R is $C_1$-$C_6$alkoxy, such as methoxy or tert-butoxy, can be made by reaction of an aldehyde of formula (IX) wherein $G^1$ is oxygen and R is $C_1$-$C_6$alkoxy, for example methoxy or tert-butoxy, with a hydroxylamine as described under 7).

12) Compounds of formula (IX) wherein $G^1$ is oxygen and R is $C_1$-$C_6$alkoxy, such as methoxy or tert-butoxy, can be prepared by reaction of a compound of formula (X) wherein $G^1$ is oxygen, R is $C_1$-$C_6$alkoxy, for example methoxy or tert-butoxy, and $X^B$ is a leaving group, for example a halogen, such as bromo, with a formylating agent, such as N,N-dimethylformamide. Such reactions are carried out in the presence of a base, for example a lithium base, such as butyl lithium, in the presence of a suitable solvent, for example a polar solvent, such as tetrahydrofuran or excess N,N-dimeth-

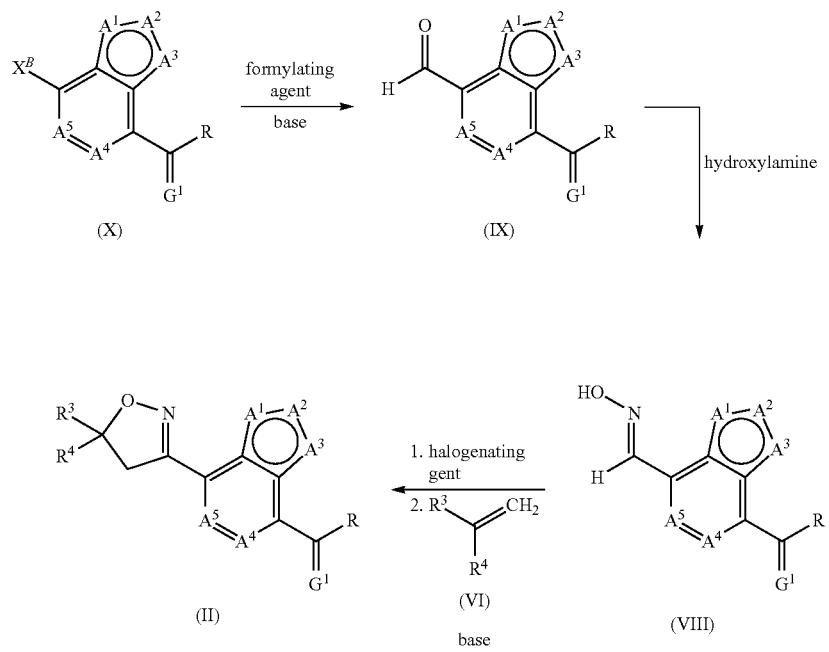

ylformamide. Compounds of formula (X) wherein $G^1$ is oxygen and R is $C_1$-$C_6$alkoxy, such as methoxy or tert-butoxy, are commercially available or can be made by methods known to a person skilled in the art.

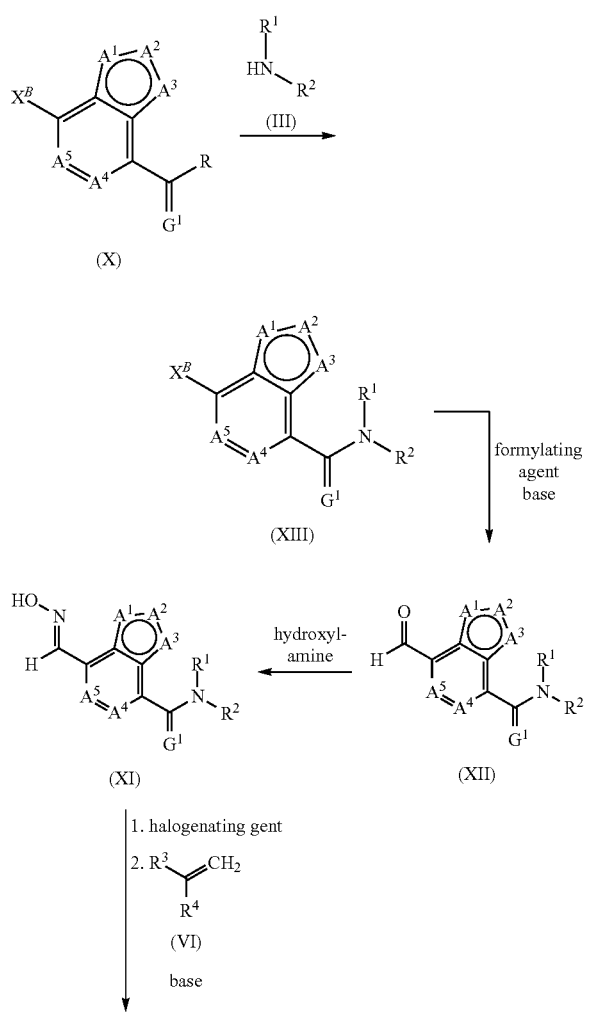

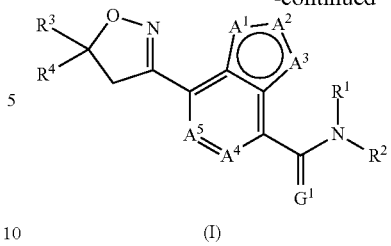

13) Alternatively, compounds of formula (I) wherein $G^1$ is oxygen, can be prepared by reaction of an oxime of formula (XI) wherein $G^1$ is oxygen, with a halogenating agent followed by a vinyl compound of formula (VI) and base as shown in Scheme 3 in a two step reaction as described under 6). The intermediate of formula (XI') wherein $G^1$ is oxygen, can optionally be isolated.

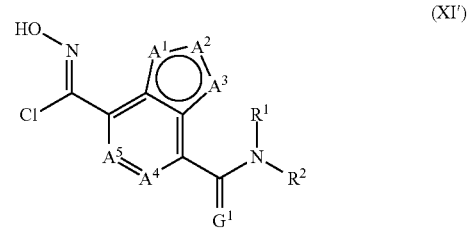

14) Compounds of formula (XI) wherein $G^1$ is oxygen, can be made by reaction of an aldehyde of formula (XII) wherein $G^1$ is oxygen, with a hydroxylamine as described under 7).

15) Compounds of formula (XII) wherein $G^1$ is oxygen, can be prepared by reaction of a compound of formula (XIII) wherein $G^1$ is oxygen and $X^B$ is a leaving group, for example a halogen, such as bromo, with a formylating agent and a base as described under 12).

16) Compounds of formula (XIII) wherein $G^1$ is oxygen and $X^B$ is a leaving group, for example a halogen, such as bromo, can be prepared by reacting an acid derivative of formula (X) wherein $G^1$ is oxygen and R is OH, $C_1$-$C_6$alkoxy or Cl, F or Br, and $X^B$ is a leaving group, for example a halogen, such as bromo, with an amine of formula (III) as described under 1).

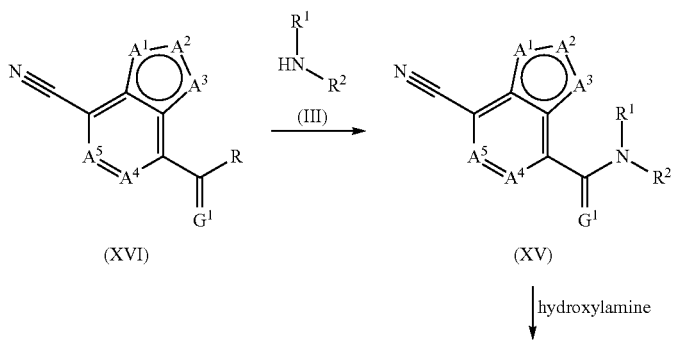

-continued

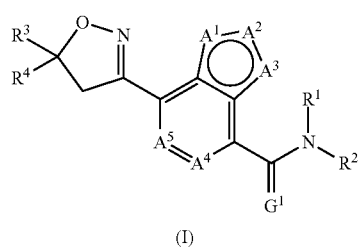
(I)

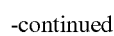
1. nitrosylating agent acid
2. 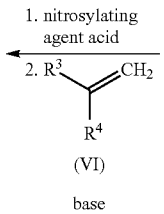
(VI)
base

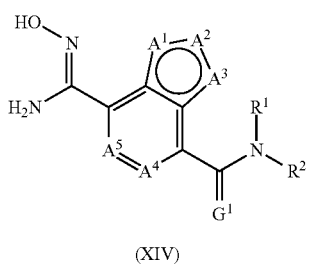
(XIV)

17) Alternatively, compounds of formula (I) wherein $G^1$ is oxygen, can be made by reaction of an N-hydroxy-amidine of formula (XIV) wherein $G^1$ is oxygen, and a vinyl compound of formula (VI) in a two step reaction as shown in Scheme 4. In the first step, the N-hydroxy-amidine of formula (XIV), wherein $G^1$ is oxygen, is reacted with a nitrosylating agent, such as sodium nitrite, in the presence of an acid, such as aqueous hydrochloric acid. The first step is carried out at a temperature of from −20° C. to +30° C., preferably from −5° C. to +10° C.

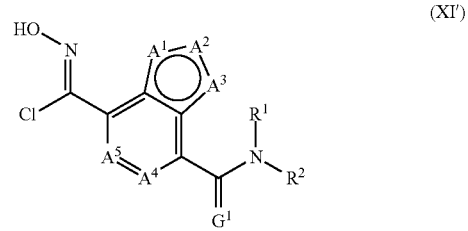
(XI')

In the second step, the chloro hydroxy imine intermediate of formula (XI') wherein $G^1$ is oxygen, is reacted with the vinyl compound of formula (VI) in the presence of a base, for example an organic base, such as triethylamine, or an inorganic base, such as sodium hydrogen carbonate, in the presence of a suitable solvent, for example a polar solvent, such as N,N-dimethylformamide or isopropanol. It is possible to conduct these two steps separately and optionally to isolate the chloro hydroxy imine intermediate or more conveniently to conduct these two steps successively in one reaction vessel without isolation of the intermediate. The second step is carried out at a temperature of from 0° C. to 100° C., preferably from 15° C. to 30° C., in particular at ambient temperature.

18) Compounds of formula (XIV) wherein $G^1$ is oxygen, can be made by reaction of a nitrile of formula (XV) wherein $G^1$ is oxygen, with a hydroxylamine as described under 7).

19) Compounds of formula (XV) wherein $G^1$ is oxygen, can be prepared by reacting an acid derivative of formula (XVI) wherein $G^1$ is oxygen and R is OH, $C_1$-$C_6$alkoxy or Cl, F or Br, with an amine of formula (III) as described under 1). Compounds of formula (XVI) wherein $G^1$ is oxygen and R is $C_1$-$C_6$alkoxy, such as methoxy or tert-butoxy, are commercially available or can be made by methods known to a person skilled in the art. Alternatively, compounds of formula (XV) wherein $G^1$ is oxygen, can be prepared by displacing the leaving group of a compound of formula (XIII) wherein $G^1$ is oxygen and $X^B$ is a leaving group, for example a halogen, such as bromo, with a cyano group.

Scheme 5

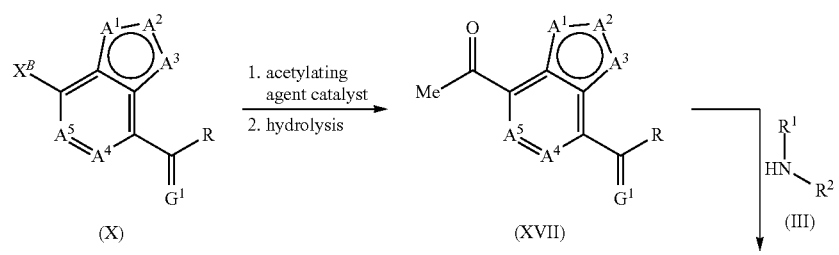

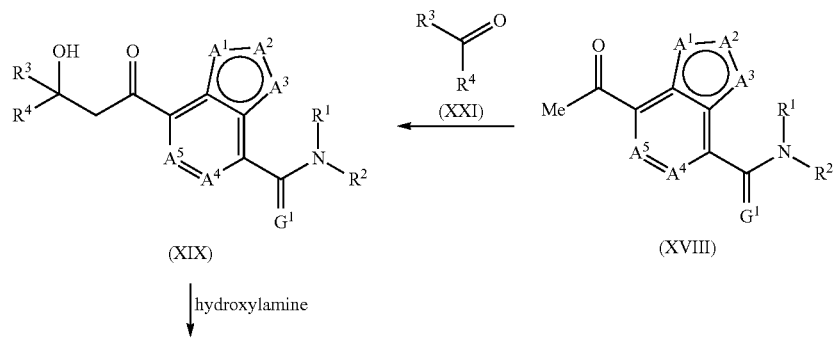

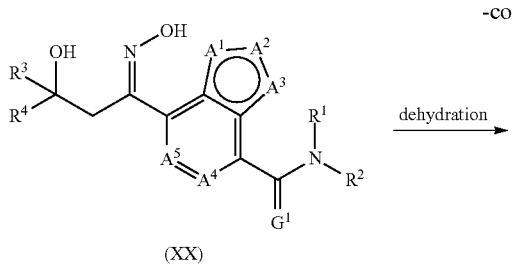 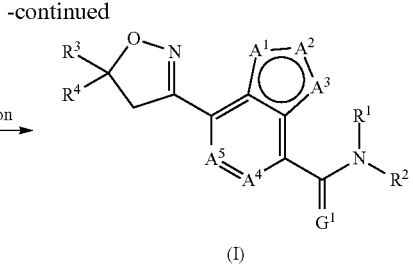

(XX) → dehydration → (I)

20) Alternatively, compounds of formula (I) wherein $G^1$ is oxygen, can be prepared by cyclisation of a compound of formula (XX) wherein $G^1$ is oxygen, as shown in Scheme 5. The cyclisation of a compound of formula (XX) can also be referred to as the dehydration of a compound of formula (XX). Such reactions are usually carried out in the presence of an acid, for example an inorganic acid, such as hydrochloric acid or sulfuric acid, or a sulfonic acid, such as methanesulfonic acid, optionally in a solvent, such as water, ethanol, or tetrahydrofuran, or a mixture thereof. The reaction is carried out at a temperature of from 0° C. to 100° C., preferably from 40° C. to 80° C. Representative experimental conditions for this transformation are described in Synthetic Communications 2003, 23, 4163-4171. Alternatively, dehydration can be carried out using a dehydrating agent, such as phosphorus pentoxide, in a solvent, such as chloroform, at a temperature of −20° C. to +50°, preferably at 0° C., as described in Journal of Heterocyclic Chemistry 1990, 27, 275. Alternatively, cyclisation can be carried out under Mitsonobu conditions involving treatment of a compound of formula (XX) with a phosphine, such as triphenylphosphine, and an azodicarboxylate reagent, such as diethyl azodicarboxylate, diisopropyl azodicarboxylate or dicyclohexyl azodicarboxylate, in a solvent, such as tetrahydrofuran, at a temperature of from 0° C. to 80° C., preferably from 0° C. to ambient temperature.

21) Compounds of formula (XX), wherein $G^1$ is oxygen, can be made by reaction of a β-hydroxy ketone of formula (XIX) wherein $G^1$ is oxygen, with a hydroxylamine as described under 7).

22) Compounds of formula (XIX) wherein $G^1$ is oxygen, can be made by aldol-type reaction of a methyl ketone of formula (XVIII) wherein $G^1$ is oxygen, with a ketone of formula (XXI). Such reactions are usually carried out in the presence of a base, such as sodium hydride, lithium hydride, lithium diisopropylamide or lithium hexamethyldisilazide, in a solvent, such as tetrahydrofuran, at a temperature of from −78° C. to +100° C., preferably from 0° C. to +80° C. Alternatively, the reaction can be performed using a Lewis acid, such as titanium tetrachloride, and an amine, such as triethylamine, diisopropylethylamine, tetramethylethylenediamine ("TMEDA") or tributylamine, in a solvent, such as dichloromethane, at a temperature of from −78° C. to ambient temperature, preferably at −78° C. Representative conditions for such a transformation are given in Tetrahedron Letters 1997, 38, 8727-8730. Ketones of formula (XXI) are commercially available or can be made by methods known to a person skilled in the art.

23) Compounds of formula (XVIII) wherein $G^1$ is oxygen, can be made by reacting an acid derivative of formula (XVII) wherein $G^1$ is oxygen and R is OH, $C_1$-$C_6$alkoxy or Cl, F or Br, with an amine of formula (III) as described under 1).

24) Compounds of formula (XVII) wherein $G^1$ is oxygen and R is $C_1$-$C_6$alkoxy, can be prepared by reacting a compound of formula (X) wherein $G^1$ is oxygen, R is $C_1$-$C_6$alkoxy and $X^B$ is a leaving group, for example a halogen, such as bromo, with an acetylating reagent, such as tributyl(1-ethoxyvinyl)tin, ethyl vinyl ether or butyl vinyl ether, in a presence of a catalyst, such as palladium(0)tetrakis(triphenylphosphine), in a solvent, such as tetrahydrofuran or toluene, at a temperature of from 60° C. to 110° C. The reaction may afford an intermediate of formula (XVII') wherein $G^1$ is oxygen, R is $C_1$-$C_6$alkoxy and R' is $C_1$-$C_6$alkyl, which can be hydrolyzed to a compound of formula (XVII). Alternatively, the reaction may yield a compound of formula (XVII) directly.

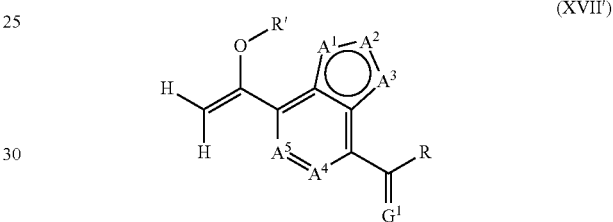

(XVII')

The hydrolysis of the intermediate of formula (XVII'), if required, is usually carried out in the presence of an acid, such as hydrochloric acid, in a solvent, such as water or ethyl acetate, or a mixture thereof, at a temperature of from 0° C. to 50° C., preferably at ambient temperature.

Scheme 6

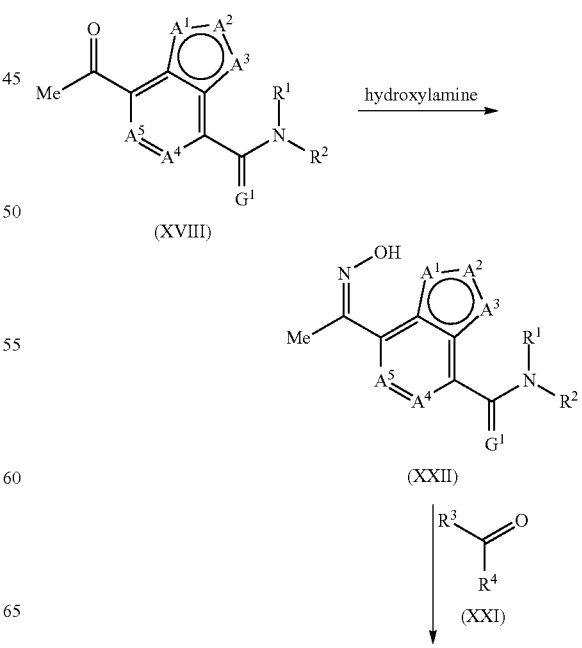

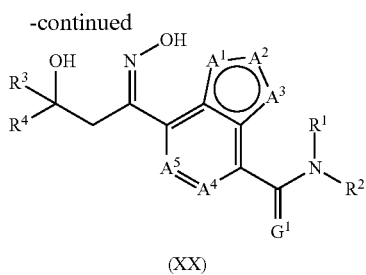

(XX)

25) Alternatively, compounds of formula (XX) wherein $G^1$ is oxygen, can be prepared by reacting a methyl oxime of formula (XXII) wherein $G^1$ is oxygen, with a ketone of formula (XXI) in an aldol-type reaction as shown in Scheme 6. Such reactions are usually carried out by treating the methyl oxime of formula (XXII) wherein $G^1$ is oxygen, with a base, such as butyl lithium, lithium diisopropylamide or lithium hexamethyldisilazide, in a solvent, such as tetrahydrofuran, at a temperature of from −78° C. to ambient temperature, preferably from −20° C. to 0° C., followed by addition of the ketone of formula (XXI) at a temperature of from −78° C. to 0° C., preferably at 0° C. Representative conditions for such a transformation can be found in Synthetic Communications 2003, 23, 4163-4171.

26) Compounds of formula (XXII) wherein $G^1$ is oxygen, can be made by reaction of a methyl ketone of formula (XVIII) wherein $G^1$ is oxygen, with a hydroxylamine as described under 7).

hydroxide, in a solvent, such as methanol, ethanol, or water, or a mixture thereof, at a temperature of from 0° C. to 100° C., preferably from ambient temperature to 80° C. Such conditions are described, for example, in J. Indian Chemical Society 1988, 65(9), 640-2. Such reactions may optionally lead to intermediates of formula (XXIV')

(XXIV')

Such intermediates can be converted into compounds of formula (I) in the presence of an acid, such as hydrochloric acid or acetic acid, or a mixture thereof, or a base, such as sodium methoxide, optionally in a solvent, such as methanol or diethyl ether, at a temperature of from 0° C. to 100° C. Representative procedures for this reaction are described in Eur. J. Org. Chem. 2002, p 1919.

28) Compounds of formula (XXIV) wherein $G^1$ is oxygen, can be obtained by various methods. For example, they can be prepared by reacting in a first step a compound of formula (XVIII) wherein $G^1$ is oxygen and Hal is a halogen, such as

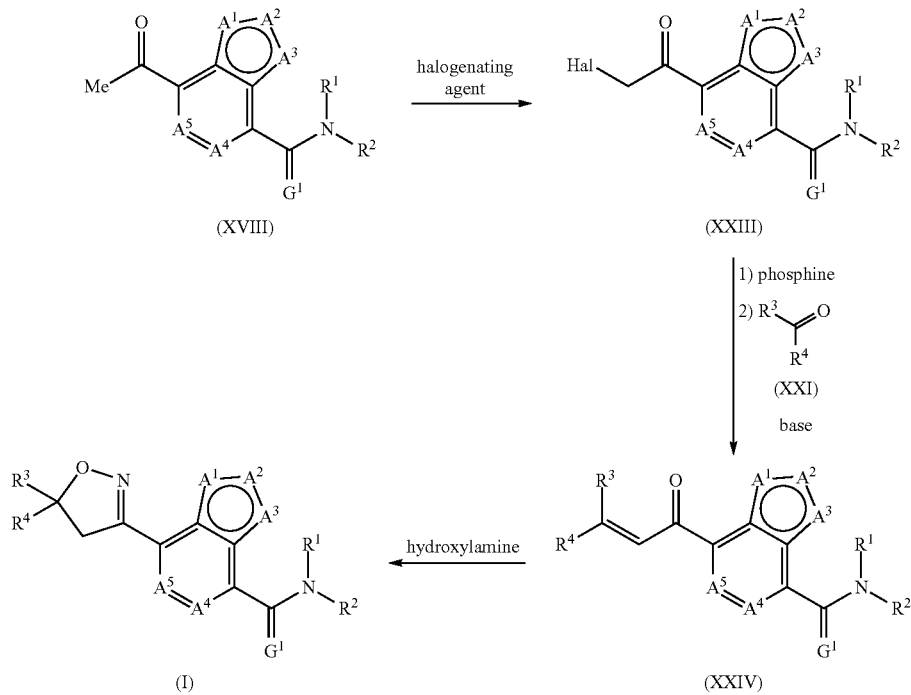

Scheme 7

27) Alternatively, compounds of formula (I) wherein $G^1$ is oxygen, can be obtained by reacting an unsaturated ketone of formula (XXIV) wherein $G^1$ is oxygen, with a hydroxylamine, such as hydroxylamine hydrochloride, as shown on Scheme 7. Such reactions can be performed optionally in the presence of a base, such as sodium hydroxide or potassium bromo or chloro, with a phosphine, such as triphenylphosphine. Such reactions are usually performed in a solvent, such as toluene, at a temperature of from ambient temperature to 150° C., preferably from 80° C. to 120° C. In a second step, the intermediate is treated with a ketone of formula (XXI) and a base, such as butyl lithium or triethylamine, in a solvent, such as tetrahydrofuran, at a temperature of from −78° C. to +100° C., preferably from ambient temperature to +80° C. Such conditions are described, for example, in Journal of Organic Chemistry 2006, 71(9), 3545-3550.

29) Compounds of formula (XVIII) wherein $G^1$ is oxygen and Hal is a halogen, such as bromo or chloro, can be prepared by reacting a methyl ketone of formula (XVIII) wherein $G^1$ is oxygen, with a halogenating agent, such as bromine or chlorine, in a solvent, such as acetic acid, at a temperature of from 0° C. to 50° C., preferably from ambient temperature to 40° C.

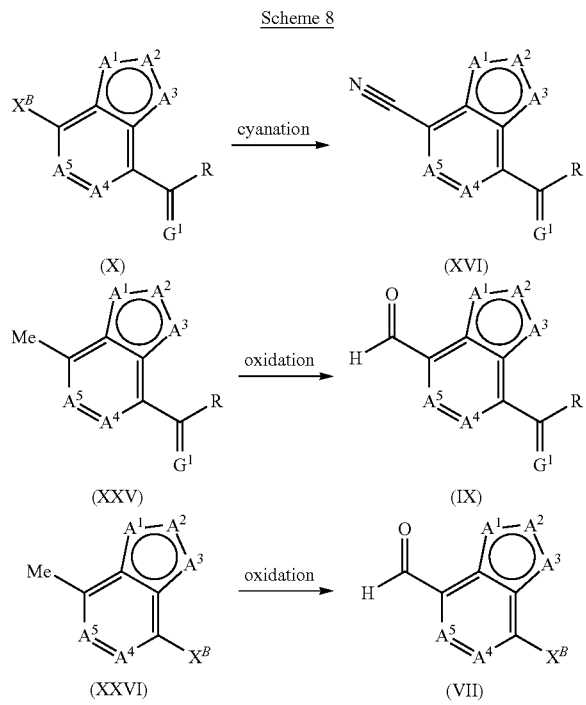

Scheme 8

30) Compounds of formula (VII), (IX), (X), (XVI), (XVII), (XXV) and (XXVI) are either known in the literature or can be made by a number methods known to a person skilled in the art. Examples of such methods are shown on Scheme 8. Thus, a compound of formula (XVI) may be obtained by cyanation of a compound of formula (X). A compound of formula (IX) may be obtained by oxidation of a compound of formula (XXV). And a compound of formula (VII) may be obtained by oxidation of a compound of formula (XXVI). The preparation of some of these compounds can be found in the preparation examples.

31) 7-Methyl-1H-benzoimidazole-4-carboxylic acid can be prepared as described in US 2004/0167194.

The compounds of formula (I) can be used to combat and control infestations of insect pests such as *Lepidoptera, Diptera, Hemiptera, Thysanoptera, Orthoptera, Dictyoptera, Coleoptera, Siphonaptera, Hymenoptera* and *Isoptera* and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

The compounds of the invention may be used for example on turf, ornamentals, such as flowers, shrubs, broad-leaved trees or evergreens, for example conifers, as well as for tree injection, pest management and the like.

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta. migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus,* and *R. santonensis*) and the *Termitidae* (for example *Globitermes* sulfureus), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds such as imidacloprid, thiacloprid, acetamiprid, nitenpyram, dinotefuran or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, spirodiclofen or spiromesifen; or s) Flubendiamid or rynaxypyr In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethyl-benzimidazole-1-sulfonamide, a-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)—N-benzyl-N([methyl (methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

Preparation Examples

The following abbreviations were used throughout this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl.

Example I1.1

Preparation of 4-bromo-7-bromomethyl-benzo[1,2,5]thiadiazole

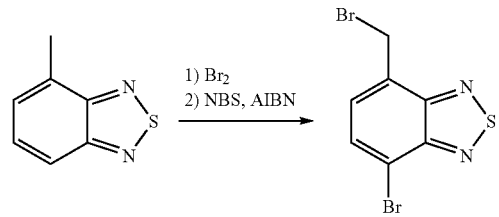

Bromine (9.78 ml) was added to a solution of 4-methyl-benzo[c][1,2,5]thiadiazole (commercially available) (15 g) in aqueous hydrobromic acid (48%) (100 ml). The reaction mixture was heated at reflux temperature for 2 hours. The reaction mixture was allowed to cool to ambient temperature and diluted with aqueous sodium metabisulfite (20 g in 250 ml water). The mixture was extracted twice with dichloromethane. The combined organic phases were washed with water and brine, dried over sodium sulfate, and concentrated to give a mixture of brominated products. This mixture was suspended in α,α,α-trifluorotoluene (250 ml) and N-bromosuccinimide ("NBS") (13.88 g) and 2,2'-azobis(2-methylpropionitrile) ("AIBN") (0.640 g) were added. The reaction mixture was heated at 90° C. for 3 hours. The reaction mixture was allowed to cool to ambient temperature and was diluted with dichloromethane (600 ml) and aqueous hydrochloric acid (1M) (300 ml). The phases were separated and the organic layer was washed successively with aqueous hydrochloric acid (1M) (2×250 ml), water (200 ml) and brine (200 ml), dried over sodium sulfate and concentrated to give 4-bromo-7-bromomethyl-benzo[1,2,5]thiadiazole (29.05 g) as a yellow solid. $^1$H-NMR (400 MHz, CDCl$_3$): 7.82 (d, 1H), 7.54 (d, 1H), 4.94 (s, 2H) ppm.

Example I1.2

Preparation of (7-bromo-benzo[1,2,5]thiadiazol-4-yl)-methanol

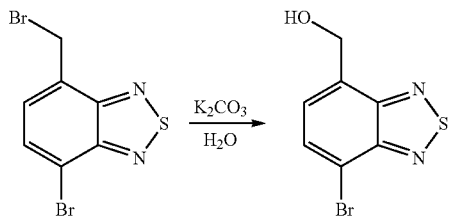

A mixture of 4-bromo-7-bromomethyl-benzo[1,2,5]thiadiazole (29.05 g) (Example II), potassium carbonate (65.2 g) and water (400 ml) was stirred at 110° C. for 16 hours. The reaction mixture was cooled to ambient temperature and quenched by addition of aqueous hydrochloric acid (2M) (400 ml). Ethyl acetate (600 ml) was added to the mixture. The phases were separated and the organic layer was washed successively with aqueous hydrochloric acid (2M) (400 ml), water (250 ml) and brine (250 ml), dried over sodium sulfate and concentrated to give (7-bromo-benzo[1,2,5]thiadiazol-4-yl)-methanol (20.22 g) as a orange solid. $^1$H-NMR (400 MHz, CDCl$_3$): 7.87 (d, 1H), 7.57 (d, 1H), 5.14 (s, 2H) ppm.

Example I1.3

Preparation of 7-bromo-benzo[1,2,5]thiadiazole-4-carbaldehyde

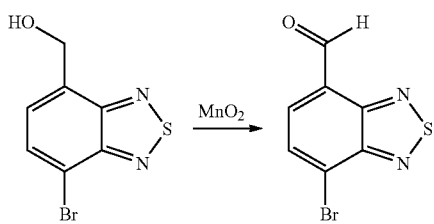

To a solution of (7-bromo-benzo[1,2,5]thiadiazol-4-yl)-methanol (20.22 g) (Example I2) in dichloromethane (185 ml) was added manganese(IV) oxide (71.7 g). The suspension was stirred at ambient temperature for 16 hours. The reaction mixture was filtered through a plug of Celite®. The filtrate was concentrated to give 7-bromo-benzo[1,2,5]thiadiazole-4-carbaldehyde (16.65 g) as an orange solid. $^1$H-NMR (400 MHz, CDCl$_3$): 10.74 (s, 1H), 8.11-8.05 (m, 2H) ppm.

Example I1.4

Preparation of 7-bromo-benzo[1,2,5]thiadiazole-4-carbaldehyde oxime

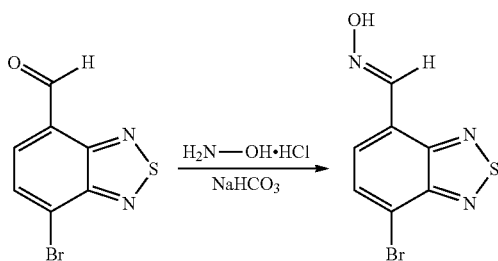

To a solution of 7-bromo-benzo[1,2,5]thiadiazole-4-carbaldehyde (16.65 g) (Example I3) in ethanol (150 ml) were added hydroxylamine hydrochloride (9.52 g), sodium hydrogen carbonate (11.51 g) and water (15 ml). The reaction mixture was stirred at ambient temperature for 16 hours. The reaction mixture was diluted with ethyl acetate (1500 ml) and water (400 ml). After separation of the phases, the aqueous layer was extracted with ethyl acetate (200 ml). The combined organic layers were washed with water (200 ml) and brine (200 ml), dried over sodium sulfate and concentrated to give 7-bromo-benzo[1,2,5]-thiadiazole-4-carbaldehyde oxime (16.65 g) as a brown solid. $^1$H-NMR (DMSO-d6, 400 MHz): 11.94 (s, 1H), 8.66 (s, 1H), 8.09-9.90 (m, 2H) ppm.

Example I1.5

Preparation of 7-bromo-N-hydroxybenzo[1,2,5]thiadiazole-4-carbimidoyl chloride

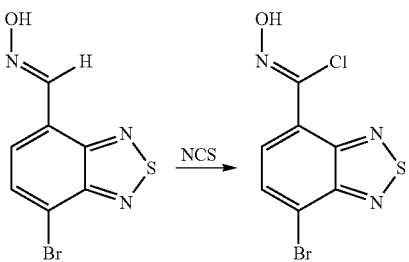

To a solution of 7-bromo-benzo[1,2,5]thiadiazole-4-carbaldehyde oxime (16.65 g) (Example I4) in N,N-dimethylformamide (150 ml) was added N-chlorosuccinimide ("NCS") (10.34 g). The reaction mixture stirred at ambient temperature for 16 hours. Water (750 ml) was added to the reaction mixture and the resulting solid was isolated by filtration to obtain 7-bromo-N-hydroxybenzo[1,2,5]thiadiazole-4-carbimidoyl chloride (15.77 g) as a yellow solid which was used without further purification.

Example I1.6

Preparation of 4-bromo-7-[5-(3,5-dichloro-phenyl)-5-trifluoromethyl-4,5-dihydro-isoxazol-3-yl]-benzo[1,2,5]thiadiazole

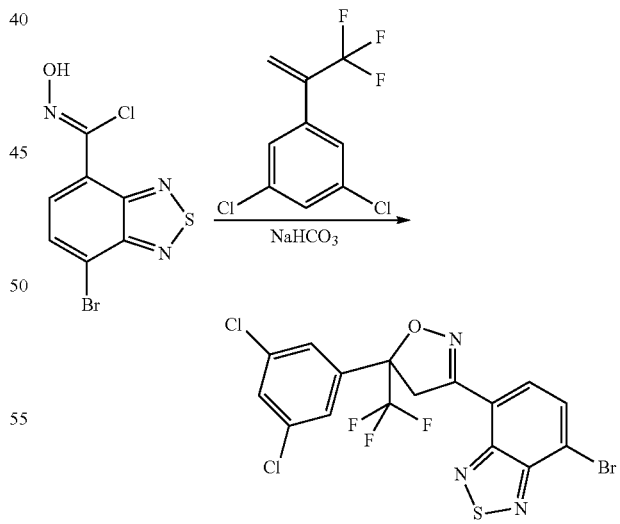

To a solution of 7-bromo-N-hydroxybenzo[1,2,5]thiadiazole-4-carbimidoyl chloride (10.01 g) (Example I5) in 2-propanol (140 ml) was added 1,3-dichloro-5-(3,3,3-trifluoro-prop-1-en-2-yl)benzene (6.87 g) (prepared according to WO 2005/085216) and sodium hydrogen carbonate (5.99 g). The reaction mixture was stirred at 65° C. for 3 hours. The reaction mixture was concentrated and the residue was purified by column chromatography (heptane/ethyl acetate 9:1) to give 4-bromo-7-[5-(3,5-dichloro-phenyl)-5-trifluoromethyl-4,5-dihydro-isoxazol-3-yl]-benzo[1,2,5]thiadiazole (7.4 g). ¹H-NMR (DMSO-d6, 400 MHz): 8.17-7.53 (m, 5H), 4.70 (d, 1H), 4.49 (d, 1H) ppm.

Example I1.7

Preparation of 7-[5-(3,5-dichloro-phenyl)-5-trifluoromethyl-4,5-dihydro-isoxazol-3-yl]-benzo[1,2,5]thiadiazole-4-carboxylic acid methyl ester

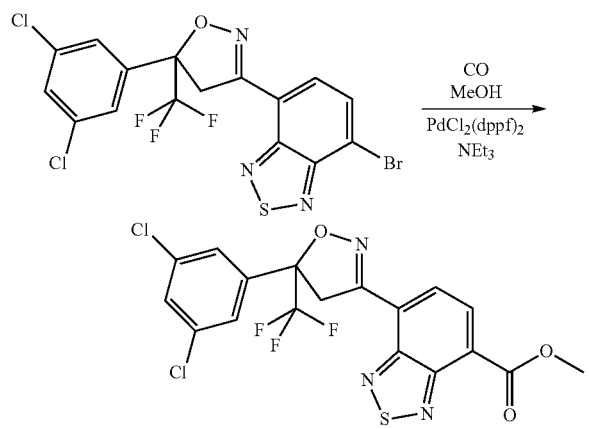

Triethylamine (7.8 ml) and methanol (72 ml) were added at ambient temperature to a solution of 4-bromo-7-[5-(3,5-dichloro-phenyl)-5-trifluoromethyl-4,5-dihydro-isoxazol-3-yl]-benzo[1,2,5]thiadiazole (7.96 g) (Example I6) in N,N-dimethylformamide (72 ml). [1,1'-Bis(diphenylphosphino)ferrocene]dichloropalladium(II) ("PdCl₂(dppf)") (654 mg) was added and the reaction mixture was stirred in a pressure reactor in an atmosphere of carbon monoxide (3 bar) at 87° C. for 16 hours. The reaction mixture was cooled to ambient temperature, filtered through a plug of Celite® and concentrated. The residue was purified by column chromatography (heptane/ethyl acetate) to give 7-[5-(3,5-dichloro-phenyl)-5-trifluoromethyl-4,5-dihydro-isoxazol-3-yl]-benzo[1,2,5]thiadiazole-4-carboxylic acid methyl ester (4.01 g) as an orange oil. ¹H-NMR (CDCl₃, 400 MHz): 8.43-7.57 (m, 5H), 4.66 (d, 1H), 4.27 (d, 1H), 4.09 (s, 3H) ppm.

Example I1.8

Preparation of 7-[5-(3,5-dichloro-phenyl)-5-trifluoromethyl-4,5-dihydro-isoxazol-3-yl]-benzo[1,2,5]thiadiazole-4-carboxylic acid

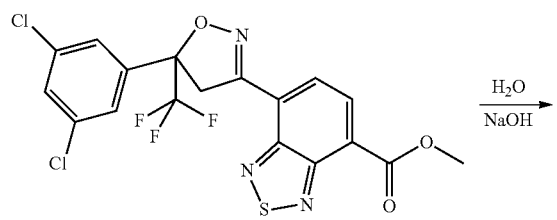

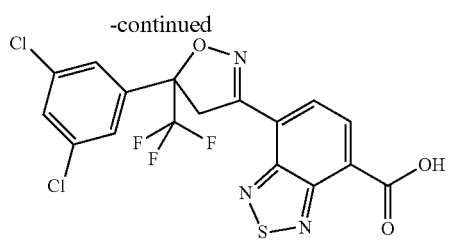

To a solution of 7-[5-(3,5-dichlorophenyl)-5-(trifluoromethyl)-4,5-dihydro-isoxazol-3-yl]-benzo[1,2,5]thiadiazole-4-carboxylic acid methyl ester (4.01 g) (Example I7) in tetrahydrofuran (30 ml) was added aqueous sodium hydroxide (1M) (25.3 ml). The reaction mixture was stirred at ambient temperature for 1.5 hours. Aqueous hydrochloric acid (1M) (100 ml) was added and the mixture diluted with ethyl acetate (150 ml). After separation of the layers, the aqueous layer was extracted with ethyl acetate (2×75 ml). The combined organic layers were washed with water (75 ml) and brine (75 ml), dried over sodium sulfate and concentrated. The residue was purified by column chromatography (dichloromethane/methanol) to give 7-[5-(3,5-dichloro-phenyl)-5-trifluoromethyl-4,5-dihydro-isoxazol-3-yl]-benzo[1,2,5]thiadiazole-4-carboxylic acid (1.29 g) as yellow solid. ¹H-NMR (DMSO-d6, 400 MHz): 13.67 (bs, 1H), 8.37-7.26 (m, 5H), 4.76 (d, 1H), 4.53 (d, 1H) ppm.

Example P1

General Method for Preparing the Compounds of the Invention in Parallel

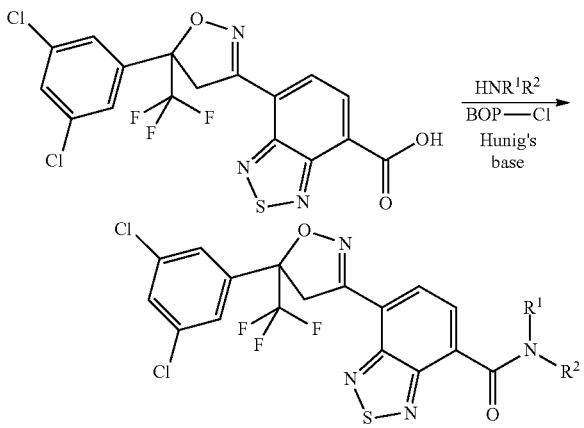

To a solution of 7-[5-(3,5-dichloro-phenyl)-5-trifluoromethyl-4,5-dihydro-isoxazol-3-yl]-benzo[1,2,5]thiadiazole-4-carboxylic acid (30 μmol) (Example I8) in N,N-dimethylacetamide ("DMA") (0.4 ml) was added successively a solution of an amine of formula HNR¹R² (30 μmol) in N,N-dimethylacetamide ("DMA") (0.145 ml), diisopropylethylamine (Hunig's Base) (0.02 ml, 100 μmol), and a solution of bis(2-oxo-3-oxazolidinyl)phosphonic chloride ("BOP-Cl") (15.3 mg) in N,N-dimethylacetamide ("DMA") (0.2 ml). The reaction mixture was stirred at 80° C. for 16 hours. Then the reaction mixture was diluted with acetonitrile (0.6 ml) and a sample was used for LC-MS analysis. The remaining mixture was further diluted with acetonitrile/N,N-dimethylformamide (4:1) (0.8 ml) and purified by HPLC. This method was used to prepare a number of compounds (Compound Nos. A1 to A24 of Table A) in parallel.

The following method was used for HPLC-MS analysis:

Method (Agilent 1100er Series) with the following HPLC gradient conditions (Solvent A: 0.1% of formic acid in water; Solvent B: 0.1% of formic acid in acetonitrile.

| Time (minutes) | A (%) | B (%) | Flow rate (ml/min) |
|---|---|---|---|
| 0 | 80 | 20 | 1.7 |
| 2.5 | 0 | 100 | 1.7 |
| 2.8 | 0 | 100 | 1.7 |
| 2.9 | 80 | 20 | 1.7 |

Type of column: Waters atlantis dc18; Column length: 20 mm; Internal diameter of column: 3 mm; Particle Size: 3 micron; Temperature: 40° C.

The characteristic values obtained for each compound were the retention time ("RT", recorded in minutes) and the molecular ion, typically the cation $MH^+$ as listed in Table A.

TABLE A

Compounds of formula (Ia):

(Ia)

| Comp No. | $R^1$ | $R^2$ | RT (min) | $MH^+$ |
|---|---|---|---|---|
| A1 | butyl- | H | 4.29 | 517 |
| A2 | 2,2,2-trifluoroethyl- | H | 4.07 | 543 |
| A3 | ethyl- | H | 3.84 | 489 |
| A4 | 1-methoxy-prop-2-yl- | H | 3.95 | 533 |
| A5 | (1H-benzimidazol-2-yl)-methyl- | H | 2.78 | 591 |
| A6 | 3,3,3-trifluoropropyl- | H | 4.11 | 557 |
| A7 | but-2-yl- | H | 4.25 | 517 |
| A8 | (tetrahydro-furan-2-yl)-methyl- | H | 3.85 | 545 |
| A9 | phenyl-methyl- | H | 4.23 | 551 |
| A10 | (2-fluoro-phenyl)-methyl- | H | 4.32 | 569 |
| A11 | 1-phenyl-eth-1-yl- | H | 4.44 | 565 |
| A12 | (4-methoxy-phenyl)-methyl- | H | 4.25 | 581 |
| A13 | 1-oxo-thietan-3-yl- | H | 3.18 | 5.49 |
| A14 | (2-chloro-pyrid-5-yl)-methyl- | H | 3.98 | 586 |
| A15 | 3-fluoro-phenyl- | H | 4.57 | 555 |
| A16 | 4-(N,N-dimethylamino-sulfonyl)-phenyl- | H | 4.29 | 644 |
| A17 | 1,3-dimethyl-1H-pyrazol-5-yl- | H | 3.80 | 555 |
| A18 | 4-methyl-thiazol-2-yl- | H | 4.30 | 558 |
| A19 | 3-methyl-thietan-3-yl- | H | 4.31 | 547 |
| A20 | 2-methyl-1-methylthio-prop-2-yl- | H | 4.48 | 563 |
| A21 | 1,1-dioxo-thietan-3-yl- | H | 5.52 | 564 |
| A22 | thietan-3-yl- | H | 4.05 | 533 |
| A23 | bicyclo[2.2.1]heptan-2-yl- | H | 4.62 | 555 |
| A24 | cyclobutyl- | H | 4.19 | 515 |

Example I2.1

Preparation of 1-amino-4-bromo-6-methy-2-nitrobenzoic acid

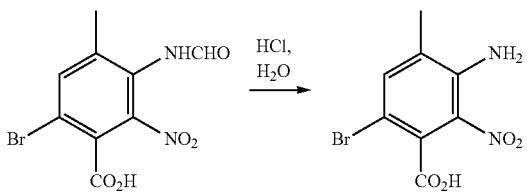

A mixture of 4-bromo-1-(formyl-amino)-6-methyl-2-nitrobenzoic acid (20 g) (prepared according to US 2004/0167194 A1), concentrated hydrochloric acid (50 ml), and water (150 ml) was heated at 50° C. for 16 h. The reaction mixture was cooled to room temperature, treated ice cold water, and extracted with ethyl acetate (3×50 ml). The combined organic layers were dried over sodium sulfate and concentrated to give 1-amino-4-bromo-6-methyl-2-nitrobenzoic acid (16 g). $^1$H-NMR (400 MHz, $CDCl_3$): 13.53 (bs, 1H), 7.56 (s, 1H), 7.07 (bs, 2H), 2.20 (s, 3H). LCMS: m/z=272.89 (M−H).

Example I2.2

Preparation of 1,2-diamino-6-methylbenzoic acid

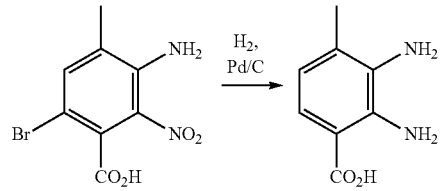

A suspension of 1-amino-4-bromo-6-methyl-2-nitrobenzoic acid (16 g) and Pd/C (3.2 g) in methanol (400 ml) was stirred under hydrogen (1 bar) for 48 h and filtered through Celite under nitrogen atmosphere. Evaporation of methanol and purification by chromatography (hexane/ethyl acetate 40:60) gave 1,2-diamino-6-methylbenzoic acid (6.7 g) as a brown solid (6.7 g). $^1$H-NMR (400 MHz, $CDCl_3$): 12.09 (bs, 1H), 6.73 (d, 1H), 6.13 (d, 1H), 1.98 (s, 3H). LCMS: m/z=167.11 (M+H)

Example I2.3

Preparation of 4-methylbenzotriazole-7-carboxylic acid

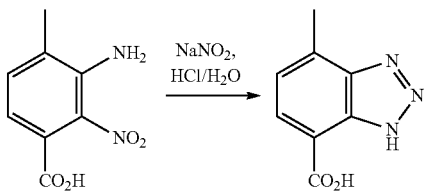

A solution of 1,2-diamino-6-methylbenzoic acid (6.7 g) in concentrated hydrochloric acid (40 ml) was cooled to 0° C., treated with sodium nitrite (2.7 g) portion wise, and stirred for 2 h. The reaction mixture was quenched with water (100 ml) and extracted with ethyl acetate (3×50 ml). The combined organic layers were dried over sodium sulfate and concentrated to give 4-methylbenzotriazole-7-carboxylic acid (5 g). $^1$H-NMR (400 MHz, DMSO): 15.77 (bs, 1H), 13.30 (bs, 1H), 7.97 (d, 1H), 7.27 (d, 1H), 2.76 (s, 3H). LCMS: m/z=178.09 (M+H).

Example I2.4

Preparation of 1,4-dimethylbenzotriazole-7-carboxylic acid methyl ester and 2,4-dimethylbenzotriazole-7-carboxylic acid methyl ester

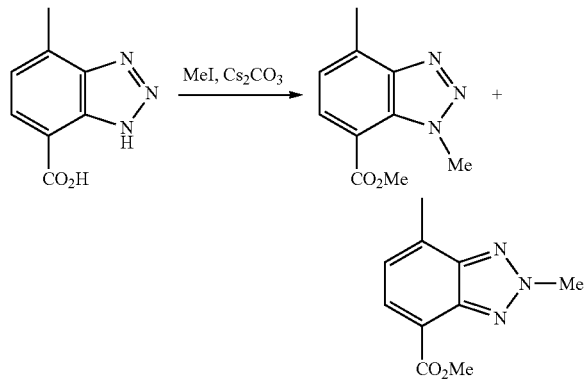

A solution of 4-methylbenzotriazole-7-carboxylic acid (0.1 g) in dimethyl formamide (20 ml) was treated with cesium carbonate (0.37 g) and methyl iodide (0.1 ml) stirred at 50° C. for 5 h. The reaction mixture was quenched with water (10 ml) and extracted with ethyl acetate (3×5 ml). The combined organic layers were dried over sodium sulfate and concentrated. Chromatographic purification (hexane/ethyl acetate 85:15) gave 1,4-dimethylbenzotriazole-7-carboxylic acid methyl ester (30 mg) and 2,4-dimethylbenzotriazole-7-carboxylic acid methyl ester (26 mg).

1,4-Dimethylbenzotriazole-7-carboxylic acid methyl ester
$^1$H-NMR (400 MHz, CDCl$_3$): 8.03 (d, 1H), 7.15 (dd, 1H), 4.57 (s, 3H), 3.97 (s, 3H), 2.81 (d, 3H). LCMS: m/z=206.03 (M+H).

2,4-Dimethylbenzotriazole-7-carboxylic acid methyl ester
$^1$H-NMR (400 MHz, CDCl$_3$): 8.07 (d, 1H), 7.21 (dd, 1H), 4.59 (s, 3H), 4.02 (s, 3H), 2.72 (d, 3H). LCMS: m/z=206.03 (M+H).

Example I2.5

Preparation of 4-formyl-1-methylbenzotriazole-7-carboxylic acid methyl ester

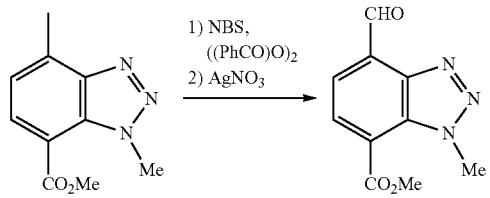 [SMILES: COC(=O)c1ccc(C)c2nnn(C)c12 ; COC(=O)c1ccc(C=O)c2nnn(C)c12]

A solution of 1,4-dimethylbenzotriazole-7-carboxylic acid methyl ester (0.1 g) in carbontetrachloride (10 ml) was treated with N-bromosuccinimide (0.5 g) and benzoyl peroxide (20 mg) and heated at 80° C. for 72 h under nitrogen atmosphere. The reaction mixture was cooled, filtered through Celite, and concentrated. The crude product (0.15 g) was directly used in the next step.

The crude product from above was dissolved in 2:1 mixture of acetone/water (6 ml), treated with silver nitrate (0.175 g), and stirred in dark condition for 16 h. The reaction mixture was concentrated to remove acetone and extracted with ethyl acetate (3×10 ml). The combined organic layers were dried over sodium sulfate and concentrated. Chromatographic purification (hexane/ethyl acetate 15:85) gave 4-formyl-1-methylbenzotriazole-7-carboxylic acid methyl ester (0.05 g) as a white solid. $^1$H-NMR (400 MHz, CDCl$_3$): 10.55 (s, 1H), 8.28 (d, 1H), 8.04 (d, 1H), 4.69 (s, 3H), 4.08 (s, 3H), 2.77 (s, 3H). GC-MS: m/z=219 (M).

Example I2.6

Preparation of 4-formyl-2-methylbenzotriazole-7-carboxylic acid methyl ester

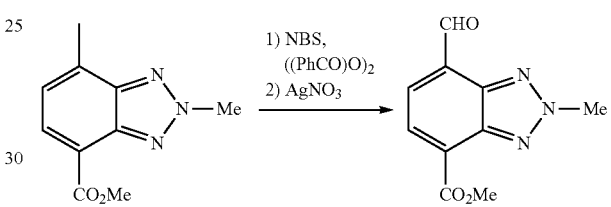

2,4-Dimethylbenzotriazole-7-carboxylic acid methyl ester (0.1 g) was converted to 4-formyl-2-methylbenzotriazole-7-carboxylic acid methyl ester (51 mg) using the same procedure as in Example I13. $^1$H-NMR (400 MHz, CDCl$_3$): 11.041 (d, 1H), 8.2 (d, 1H), 7.96 (d, 1H), 4.63 (s, 3H), 4.04 (s, 3H), 2.77 (s, 3H). LC-MS: m/z=220 (M+H).

Example I2.7

Preparation of 1-methyl-6-methoxycarbonylbenzotriazole-4-carbaldehyde oxime

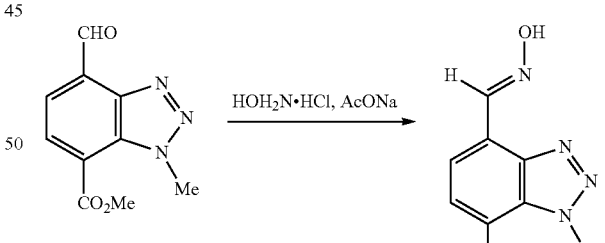

A solution of 4-formyl-1-methylbenzotriazole-7-carboxylic acid methyl ester (0.15 g) in isopropyl alcohol (10 ml) and water (5 ml) was treated with hydroxylamine hydrochloride (0.05 g) and sodium acetate (0.06 g) and stirred for 2 h. Isopropyl alcohol was removed and the remaining mixture was extracted with ethyl acetate (3×5 ml). The combined organic layers were dried over sodium sulfate and concentrated to give 1-methyl-6-methoxycarbonylbenzotriazole-4-carbaldehyde oxime (0.14 g). $^1$H-NMR (400 MHz, DMSO): 12.06 (s, 1H), 8.55 (s, 1H), 8.11 (d, 1H), 7.79 (d, 1H), 4.57 (s, 3H), 3.93 (s, 3H). LC-MS: m/z=235.08 (M+H).

Example I2.8

Preparation of 2-methyl-6-methoxycarbonylbenzotriazole-4-carbaldehyde oxime

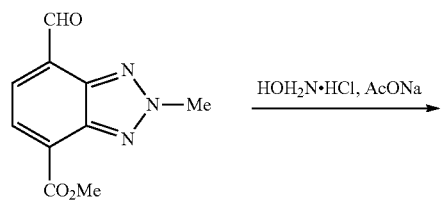

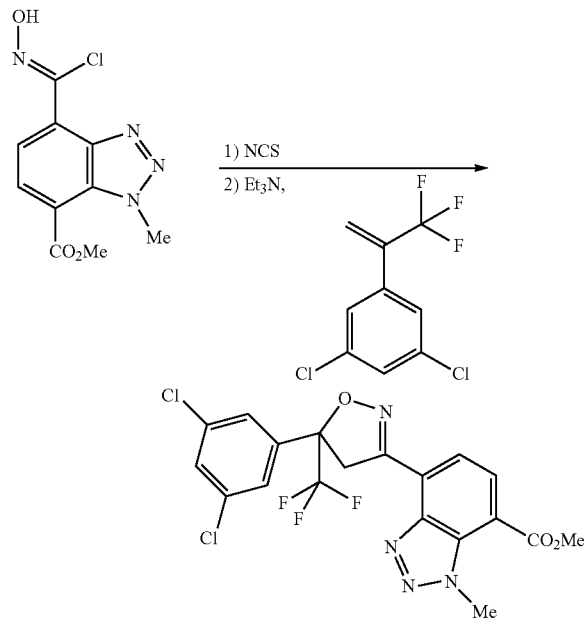

4-Formyl-2-methylbenzotriazole-7-carboxylic acid methyl ester (0.15 g) was converted to 2-methyl-6-methoxycarbonylbenzotriazole-4-carbaldehyde oxime (0.142 g) using the same procedure as in Example I15. $^1$H-NMR (400 MHz, DMSO): 12.06 (s, 1H), 8.55 (s, 1H), 8.11 (d, 1H), 7.79 (d, 1H), 4.57 (s, 3H), 3.93 (s, 3H). LC-MS: m/z=235.06 (M+H).

Example I2.9

Preparation of 3-methyl-4-methoxycarbonyl-7-[5-(3,5-dichloro-phenyl)-5-trifluoromethyl-4,5-dihydro-isoxazol-3-yl]-benzotriazole A solution of 1-methyl-6-methoxycarbonylbenzotriazole-4-carbaldehyde oxime (0.1 g) in dimethyl formamide (10 ml) was treated with N-chlorosuccinimide (0.17 g) and stirred at 40° C. for 2 h under nitrogen atmosphere. Then reaction mixture was cooled to room temperature and treated with 1,3-dichloro-5-(3,3,3-trifluoroprop-1-en-2-yl)benzene (0.47 g) (prepared according to WO 2005/085216) and triethylamine (0.02 ml), stirred at room temperature for 16 h under nitrogen atmosphere, and treated with water (50 ml). The mixture was extracted with ethyl acetate (3×10 ml) and the combined organic layers were dried over sodium sulfate. Evaporation of solvents and purification by column chromatograph gave 3-methyl-4-methoxycarbonyl-7-[5-(3,5-dichloro-phenyl)-5-trifluoromethyl-4,5-dihydro-isoxazol-3-yl]-benzotriazole (85 mg). $^1$H-NMR (400 MHz, CDCl$_3$): 8.15 (d, 1H), 8.05 (d, 1H), 7.58 (d, 2H), 7.42 (t, 1H), 4.74 (bd, 1H), 4.60 (s, 1H), 4.38 (bd, 1H), 4.02 (s, 3H). LC-MS: m/z=472.96 (M+H).

Example I2.10

Preparation of 2-methyl-4-methoxycarbonyl-7-[5-(3,5-dichloro-phenyl)-5-trifluoromethyl-4,5-dihydro-isoxazol-3-yl]-benzotriazole

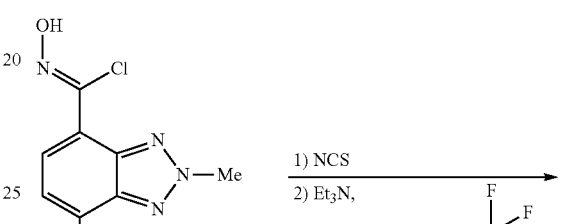

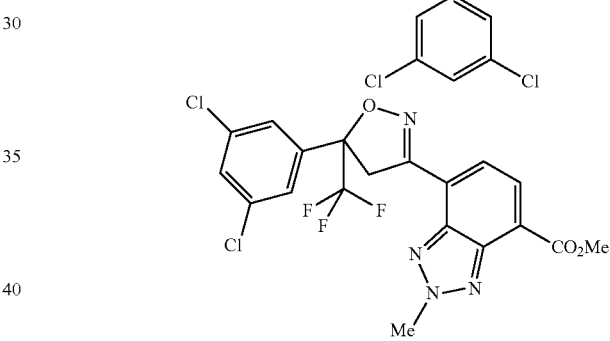

2-Methyl-6-methoxycarbonylbenzotriazole-4-carbaldehyde oxime (0.1 g) was converted to 2-methyl-4-methoxycarbonyl-7-[5-(3,5-dichloro-phenyl)-5-trifluoromethyl-4,5-dihydro-isoxazol-3-yl]-benzotriazole (750 mg) using the same procedure as in Example I17. $^1$H-NMR (400 MHz, CDCl$_3$): 8.18 (d, 1H), 7.94 (d, 1H), 7.56 (d, 2H), 7.43 (t, 1H), 4.66 (s, 1H), 4.50 (bd, 1H), 4.07 (s, 3H). LC-MS: m/z=472.99 (M+H).

Example I2.11

Preparation of 3-methyl-7-[5-(3,5-dichloro-phenyl)-5-trifluoromethyl-4,5-dihydro-isoxazol-3-yl]-benzotriazole-4-carboxylic acid

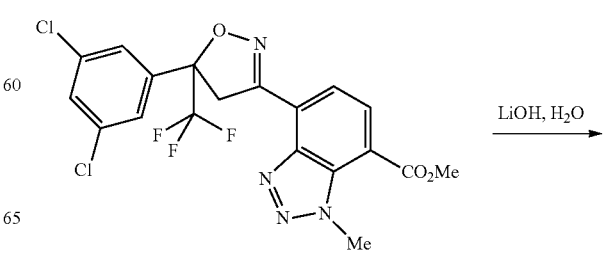

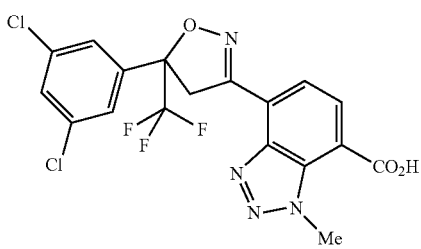

A solution of 3-methyl-4-methoxycarbonyl-7-[5-(3,5-dichloro-phenyl)-5-trifluoromethyl-4,5-dihydro-isoxazol-3-yl]-benzotriazole (0.1 g), lithiumhydroxide (11 mg) in tetrahydrofuran (10 ml) and water (5 ml) was stirred for 30 minutes. Tetrahydrofuran was removed and extracted with ethyl acetate (3×5 ml). The combined organic layers were dried over sodium sulfate and concentrated to give 3-methyl-7-[5-(3,5-dichloro-phenyl)-5-trifluoromethyl-4,5-dihydro-isoxazol-3-yl]-benzotriazole-4-carboxylic acid. $^1$H-NMR (400 MHz, DMSO): 7.80 (t, 1H), 7.73 (d, 1H), 7.69 (d, 1H), 7.62 (d, 1H), 4.74 (bd, 1H), 4.50 (s, 3H), 4.46 (bd, 1H). LC-MS: m/z=458.98 (M+H).

Example I2.12

Preparation of 2-methyl-7-[5-(3,5-dichloro-phenyl)-5-trifluoromethyl-4,5-dihydro-isoxazol-3-yl]-benzotriazole-4-carboxylic acid

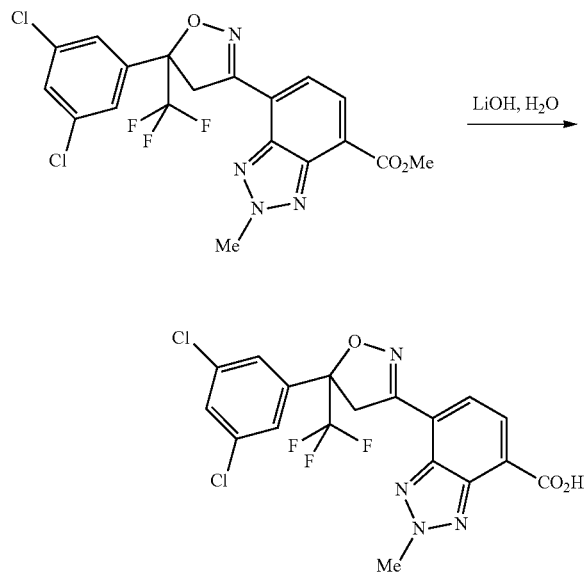 [SMILES: COC(=O)c1ccc(C2=NOC(c3cc(Cl)cc(Cl)c3)(C(F)(F)F)C2)c2nn(C)nc12 ; Cn1nc2c(C(=O)O)ccc(C3=NOC(c4cc(Cl)cc(Cl)c4)(C(F)(F)F)C3)c2n1]

2-Methyl-4-methoxycarbonyl-7-[5-(3,5-dichloro-phenyl)-5-trifluoromethyl-4,5-dihydro-isoxazol-3-yl]-benzotriazole (0.1 g) was converted to 2-methyl-7-[5-(3,5-dichloro-phenyl)-5-trifluoromethyl-4,5-dihydro-isoxazol-3-yl]-benzotriazole-4-carboxylic acid (81 mg) using the same procedure as in Example I19. $^1$H-NMR (400 MHz, DMSO): 13.53 (bs, 1H), 8.10 (m, 1H), 7.88 (d, 1H), 7.81 (t, 1H), 7.69 (m, 2H), 4.64 (d, 1H), 4.61 (s, 3H), 4.44 (d, 1H).

Example P2.1

General Method for Preparing the Compounds of the Invention in Parallel

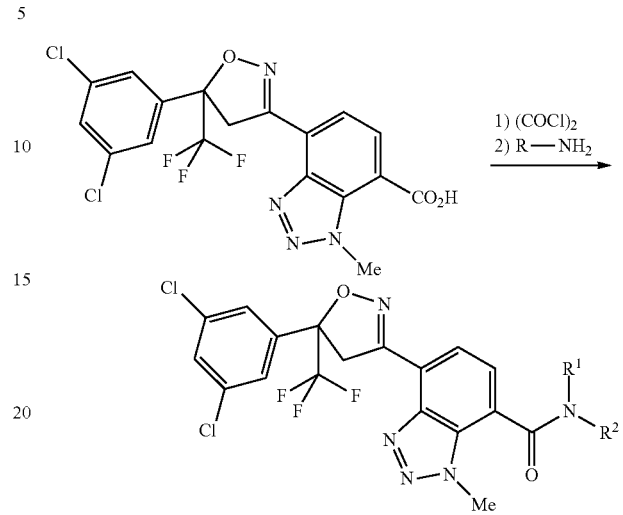

Oxalyl chloride (0.2 ml) was added drop wise to a solution of 3-methyl-7-[5-(3,5-dichloro-phenyl)-5-trifluoromethyl-4,5-dihydro-isoxazol-3-yl]-benzotriazole-4-carboxylic acid (0.1 g) in tetrahydrofuran (5 ml) and 1 drop of N,N-dimethylformamide and stirred at room temperature under nitrogen atmosphere for 4 h. The mixture was concentrated and dissolved in tetrahydrofuran (10 ml), treated with an amine of formula HNR$^1$R$^2$ (2 equivalents), triethylamine (1 equivalent) and stirred for 16 h under nitrogen atmosphere. The reaction mixture was concentrated and purified by chromatography. This method was used to prepare a number of compounds.

Example P2.2

General Method for Preparing the Compounds of the Invention in Parallel

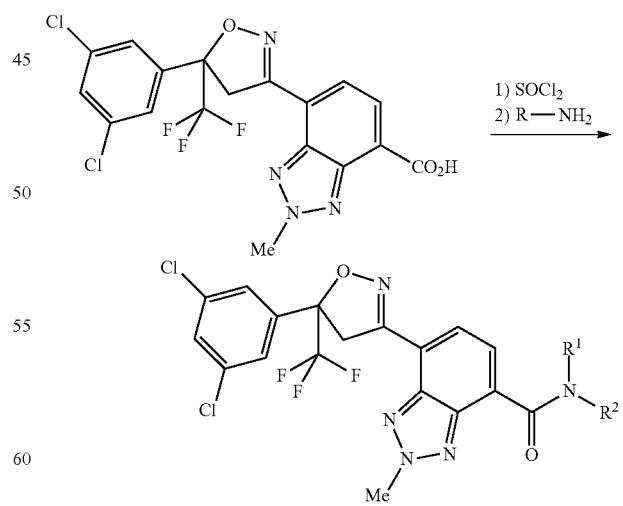

2-methyl-7-[5-(3,5-dichloro-phenyl)-5-trifluoromethyl-4,5-dihydro-isoxazol-3-yl]-benzotriazole-4-carboxylic acid was converted to a number of compounds of type if according to the procedure as in Example P2.1.

The following method was used for HPLC-MS analysis:

Method (Agilent 1200er Series) with the following HPLC gradient conditions (Solvent A: 0.1% of formic acid in water; Solvent B: 0.1% of formic acid in acetonitrile).

| Time (minutes) | A (%) | B (%) | Flow rate (ml/min) |
|---|---|---|---|
| 0 | 90 | 10 | 1.0 |
| 7.0 | 5 | 95 | 1.0 |
| 7.5 | 0 | 100 | 1.0 |
| 12.0 | 0 | 100 | 1.0 |

Type of column: Eclipse (XBD-c18) Column length: 150 mm; Internal diameter of column: 4.5 mm; Particle Size: 5 micron; Temperature: 40° C.

The characteristic values obtained for each compound were the retention time ("RT", recorded in minutes) and the molecular ion, typically the cation MH$^+$ as listed in Tables B and C.

TABLE B

Compounds of formula (Ie):

(Ie)

| Comp No. | R$^1$ | R$^2$ | RT (min) | MH$^+$ |
|---|---|---|---|---|
| B1 | butyl- | H | 4.75 | 514 |
| B2 | 2,2,2-trifluoroethyl- | H | 4.70 | 540 |
| B3 | cyclobutyl- | H | 4.68 | 512 |

TABLE C

Compounds of formula (If):

(If)

| Comp No. | R$^1$ | R$^2$ | RT (min) | MH$^+$ |
|---|---|---|---|---|
| C1 | butyl- | H | 4.84 | 514 |
| C2 | 2,2,2-trifluoroethyl- | H | 4.72 | 540 |
| C3 | thietan-3-yl- | H | 4.78 | 530 |
| C4 | cyclobutyl- | H | 4.77 | 512 |

Example I3.1

Preparation of 3,4-dimethyl-2-nitrobenzoic acid

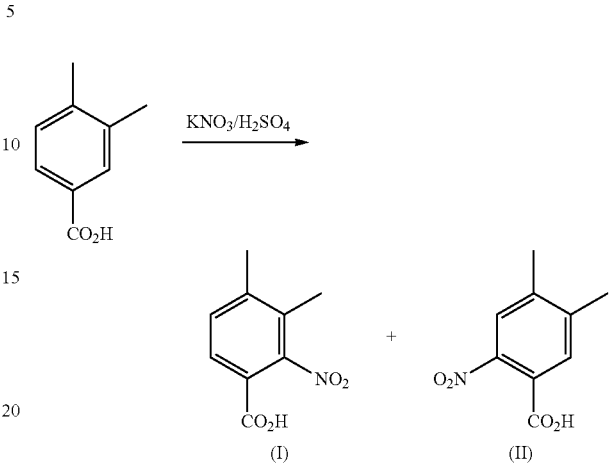

A solution of 3,4-dimethylbenzoic acid (40 g) in concentrated sulphuric acid (250 ml) was cooled to 0° C., treated with a solution of potassium nitrite (27 g) in sulphuric acid (100 ml) dropwise over a period of 1 h, and stirred for 2 h. The reaction mixture was quenched with ice cooled water (100 ml). The solid precipitated was filtered, dissolved in water (2 l), basified with 2N aqueous sodium hydroxide. The solution was acidified to pH 4 with 2N aqueous hydrochloric acid and filtered to get 3,4-dimethyl-5-nitrobenzoic acid (II) (25 g) as colorless solid. The filtrate was further acidified to pH 3 and filtered get 3,4-dimethyl-2-nitrobenzoic acid (I) (13 g) as colorless solid.

3,4-dimethyl-2-nitrobenzoic acid (I): $^1$H-NMR (400 MHz, CDCl$_3$): 2.11 (s, 3H), 2.49 (s, 3H), 7.51 (d, 1H), 7.97 (d, 1H), 7.76 (d, 1H).

3,4-dimethyl-5-nitrobenzoic acid (II): $^1$H-NMR (400 MHz, CDCl$_3$): 2.72 (s, 6H), 7.50 (s, 1H), 7.76 (s, 1H).

Example I3.2

Preparation of methyl 3,4-dimethyl-2-nitrobenzoate

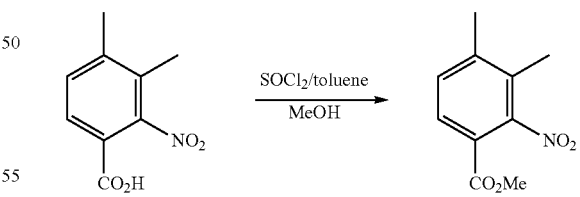

A solution of 3,4-dimethyl-2-nitrobenzoic acid (13 g) and thionyl chloride (11.8 g) in toluene (100 ml) was refluxed for 4 h. The reaction mixture was cooled at 0° C., treated with methanol (15 ml) and the solvent was removed under vacuum. The reaction mixture was treated water (50 ml) and extracted with ethyl acetate (3×50 ml). The combined organic layers were dried over sodium sulfate and concentrated to give methyl 3,4-dimethyl-2-nitrobenzoate (10 g). $^1$H-NMR (400 MHz, CDCl$_3$): 2.19 (s, 3H), 2.38 (s, 3H), 3.87 (s, 3H), 7.25 (d, 1H), 7.79 (d, 1H).

Example I3.3

Preparation of methyl 3,4-dimethyl-2-aminobenzoate

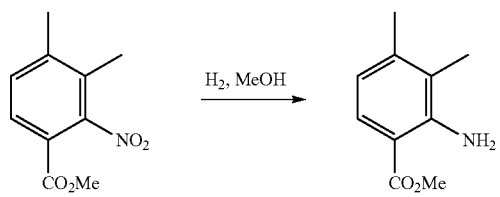

A suspension of methyl 3,4-dimethyl-2-nitrobenzoate (23 g) and Pd/C (2.3 g) in methanol (400 ml) was stirred under hydrogen (1 bar) for 48 h and filtered through Celite under nitrogen atmosphere. Evaporation of methanol gave methyl 3,4-dimethyl-2-aminobenzoate (20 g). $^1$H-NMR (400 MHz, CDCl$_3$): 7.67 (d, 1H), 6.6 (d, 1H), 3.86 (s, 3H), 2.27 (s, 3H), 2.1 (s, 3H).

Example I3.4

Preparation of 4-methyl-1H-indazole-7-carboxylic acid methyl ester

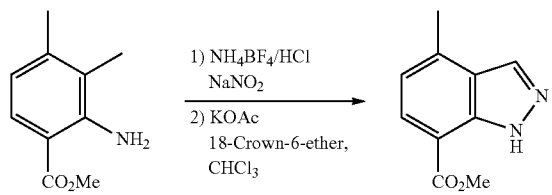

A solution of methyl 3,4-dimethyl-2-aminobenzoate (10 g) in concentrated hydrochloric acid (20 ml) was cooled to 0° C., treated with solution of tetrafluoroammoniumborate (9.4 g) in water (2 ml), a solution of sodium nitrite (7.7 g) in water (2 ml) dropwise, stirred for 2 h, filtered to get a solid. The solid residue was dissolved in chloroform (50 m), treated with potassium acetate (2 mol equivalents) and catalytic amounts of 18-Crown-6, and stirred for 12 h. The reaction mixture was treated with water (50 ml) and extracted with chloroform (2×50 ml). The combined organic layers were dried over sodium sulfate and concentrated. Chromatographic purification (hexane/ethyl acetate 80:20) gave 4-methyl-1H-indazole-7-carboxylic acid methyl ester (3.2 g). $^1$H-NMR (400 MHz, CDCl$_3$): 2.68 (s, 3H), 4.00 (s, 3H), 7.02 (d, 1H), 7.97 (d, 1H), 8.15 (s, 1H). LC-MS (methanol): m/z=191 (M+H).

Example I3.5

Preparation of 1,4-dimethyl-1H-indazole-7-carboxyl acid methyl ester

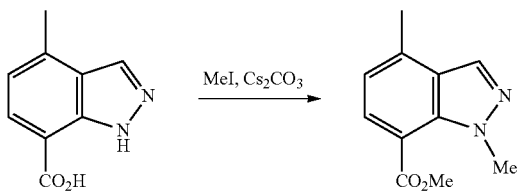

A solution of 4-methyl-1H-indazole-7-carboxylic acid methyl ester (6 g) in acetonitrile (100 ml) was treated with cesium carbonate (21 g) and methyl iodide (4.9 ml) and stirred at 50° C. for 8 h. The reaction mixture was concentrated, treated with water (10 ml), and extracted with ethyl acetate (3×50 ml). The combined organic layers were dried over sodium sulfate and concentrated. Chromatographic purification (hexane/ethyl acetate 90:10) gave 1,4-dimethyl-1H-indazole-7-carboxyl acid methyl ester (4.2 g). $^1$H-NMR (400 MHz, CDCl$_3$): 2.62 (s, 3H), 3.96 (s, 3H), 4.27 (s, 3H), 6.92 (d, 1H), 7.87 (d, 1H), 8.05 (s, 1H).

Example I3.6

Preparation of 4-formyl-1-methyl-1H-indazole-7-carboxylic acid methyl ester

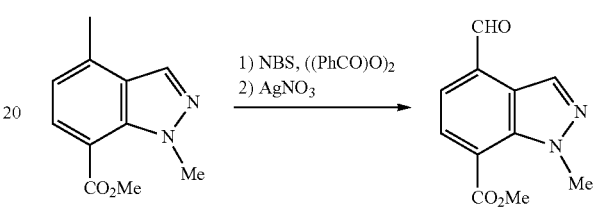

A solution of 1,4-dimethyl-1H-indazole-7-carboxyl acid methyl ester (4.2 g) in carbontetrachloride (100 ml) was treated with N-bromosuccinimide (14.4 g) and benzoyl peroxide (110 mg) and heated at 90° C. for 16 h under nitrogen atmosphere. The reaction mixture was cooled, filtered through Celite, and concentrated. The crude product (10 g) was directly used in the next step. The crude product was dissolved in 2:1 mixture of acetone/water (100 ml), treated with silver nitrate (8.5 g), and stirred in dark condition for 12 h. The reaction mixture was concentrated to remove acetone and extracted with ethyl acetate (3×50 ml). The combined organic layers were dried over sodium sulfate and concentrated. Chromatographic purification (hexane/ethyl acetate 10:90) gave 4-formyl-1-methyl-1H-indazole-7-carboxylic acid methyl ester (1.5 g) as a white solid. $^1$H-NMR (400 MHz, CDCl$_3$): 10.26 (s, 1H), 8.72 (s, 1H), 7.68 (d, 1H), 7.25 (d, 1H), 4.26 (s, 1H), 4.03 (s, 3H). LC-MS (methanol): m/z=219 (M+H).

Example I3.7

Preparation of 4-(hydroxyimino-methyl-1-methyl-1H-indazole-7-carboxylic acid methyl ester

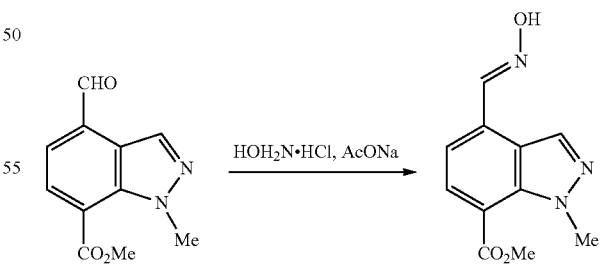

A solution of 4-formyl-1-methyl-1H-indazole-7-carboxylic acid methyl ester (1.4 g) in isopropyl alcohol (30 ml) and water (20 ml) was treated with hydroxylamine hydrochloride (0.62 g) and sodium acetate (0.72 g) and stirred for 4 h. Isopropyl alcohol was removed and the remaining mixture was extracted with ethyl acetate (2×50 ml). The combined organic layers were dried over sodium sulfate and concentrated to give 4-(hydroxyimino-methyl-1-methyl-1H-indazole-7-carboxylic acid methyl ester (1.5 g). $^1$H-NMR (400 MHz, DMSO): 10.1 (s, 1H), 8.5 (s, 1H), 8.4 (s, 1H), 7.8 (d, 1H), 7.1 (d, 1H), 4.20 (s, 3H), 4.00 (s, 3H).

Example I3.8

Preparation of 4-[5-(3,5-dichlotophenyl)-5-trifluoromethyl-4,5-dihydro-isoxazol-3-yl]-1-methyl-1H-indazole-7-carboxylic acid methyl ester]

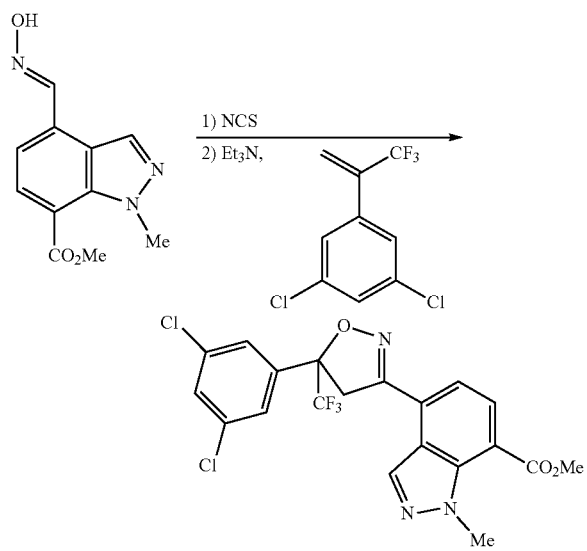

A solution of 4-(hydroxyimino-methyl-1-methyl-1H-indazole-7-carboxylic acid methyl ester (1.4 g) in dimethyl formamide (50 ml) was treated with N-chlorosuccinimide (0.85 g) and stirred at 50° C. for 3 h under nitrogen atmosphere. Then reaction mixture was cooled to room temperature and treated with 1,3-dichloro-5-(3,3,3-trifluoroprop-1-en-2-yl)benzene (1.43 g) (prepared according to WO 2005/085216) and triethylamine (0.8 ml), stirred at room temperature for 16 h under nitrogen atmosphere, and treated with water (50 ml). The solid appeared was filtered and purified by column chromatograph (hexane/ethyl acetate 20:80) to give 4-[5-(3,5-dichlorophenyl)-5-trifluoromethyl-4,5-dihydro-isoxazol-3-yl]-1-methyl-1H-indazole-7-carboxylic acid methyl ester (1.1 g). $^1$H-NMR (400 MHz, DMSO): 8.47 (s, 1H), 7.95 (d, 1H), 7.82 (d, 1H), 7.68 (s, 2H), 7.51 (d, 1H), 4.52 (dd, 2H), 4.09 (s, 3H), 3.97 (s, 3H). LC-MS (methanol): m/z=471 (M+H).

Example I3.9

Preparation of 4-[5-(3,5-dichlotophenyl)-5-trifluoromethyl-4,5-dihydro-isoxazol-3-yl]-1-methyl-1H-indazole-7-carboxylic acid

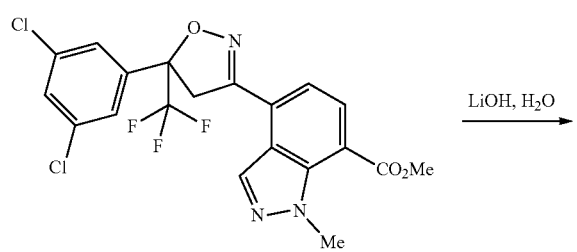

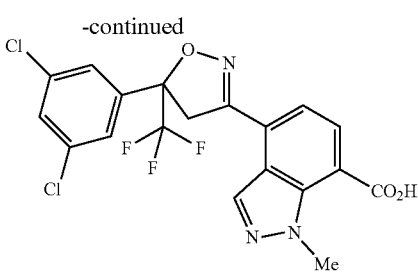

A solution of 4-[5-(3,5-dichlorophenyl)-5-trifluoromethyl-4,5-dihydro-isoxazol-3-yl]-1-methyl-1H-indazole-7-carboxylic acid methyl ester (0.7 g), lithiumhydroxide (93 mg) in tetrahydrofuran (20 ml) and water (10 ml) was stirred for 1 h. Tetrahydrofuran was removed, and the residue was treated with 2N aqueous hydrochloric acid to get a solid precipitate. Filtration and drying gave 4-[5-(3,5-dichlotophenyl)-5-trifluoromethyl-4,5-dihydro-isoxazol-3-yl]-1-methyl-1H-indazole-7-carboxylic acid as white solid. $^1$H-NMR (400 MHz, DMSO): 8.45 (s, 1H), 7.92 (d, 1H), 7.80 (s, 1H), 7.68 (s, 2H), 7.49 (d, 1H), 4.51 (dd, 2H), 4.18 (s, 3H). LC-MS (methanol): m/z=457.87 (M+H).

Example P3

General Method for Preparing the Compounds of the Invention in Parallel

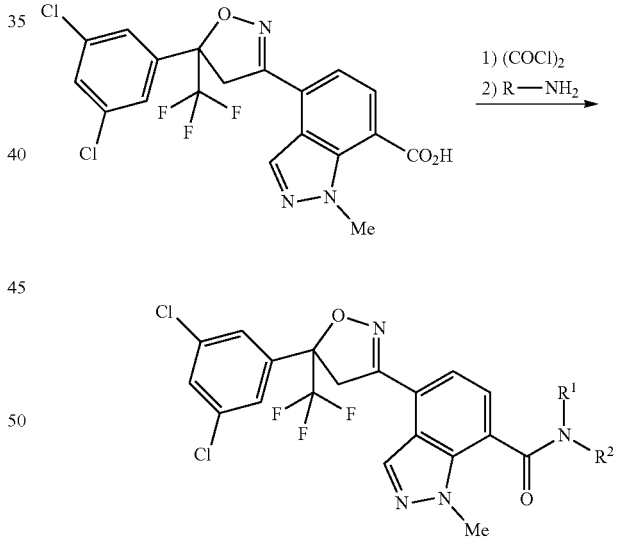

Oxalyl chloride (0.2 ml) was added drop wise to a solution of 4-[5-(3,5-dichlotophenyl)-5-trifluoromethyl-4,5-dihydro-isoxazol-3-yl]-1-methyl-1H-indazole-7-carboxylic acid (0.1 g) in tetrahydrofuran (5 ml) and 1 drop of N,N-dimethylformamide and stirred at room temperature under nitrogen atmosphere for 4-6 h. The mixture was concentrated and dissolved in tetrahydrofuran (10 ml), treated with an amine of formula HNR$^1$R$^2$ (2 equivalents), triethylamine (1 equivalent) and stirred for 16 h under nitrogen atmosphere. The reaction mixture was concentrated and purified by chromatography. This method was used to prepare a number of compounds.

TABLE D

Compounds of formula (Ig):

(Ig)

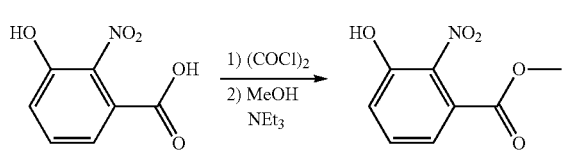

| Comp No. | $R^1$ | $R^2$ | NMR data |
|---|---|---|---|
| D1 | thietan-3-yl- | H | 1H-NMR (400 MHz, CDCl$_3$): 8.50 (d, 1H), 7.55 (s, 2H), 7.44 (s, 1H), 7.34 (d, 1H), 7.02 (d, 1H), 6.74 (d, 1H), 5.49 (m, 1H), 4.20 (d, 1H), 4.08 (s, 3H), 3.81 (d, 1H), 3.50 (m, 4H). LC-MS (methanol): m/z = 526.81 (M + H). |
| D2 | cyclobutyl- | H | 1H-NMR (400 MHz, DMSO): 9.06 (s, 1H), 8.39 (s, 1H), 7.82 (s, 1H), 7.69 (s, 2H), 7.50 (d, 1H), 7.46 (d, 1H), 4.46 (m, 3H), 4.03 (s, 3H), 2.29 (m, 2H), 2.06 (m, 2H), 1.71 (m, 2H). LC-MS (methanol): m/z = 510.98 (M + H). |

Example I4.1

Preparation of 3-hydroxy-2-nitro-benzoic acid methyl ester

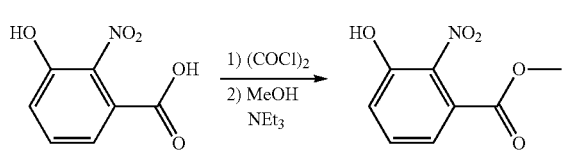

3-Hydroxy-2-nitro-benzoic acid (commercially available) (31.5 g) was suspended in acetonitrile (100 ml). Oxalyl chloride (22 ml) in acetonitrile (20 ml) was added dropwise upon which a vigorous gas stream evolved. After 15 minutes the reaction slowed down and therefore, the reaction mixture was heated with a warm water bath (40° C.) for 40 minutes. The mixture was concentrated and the residue was re-dissolved in dichloromethane (100 ml). A mixture of methanol (50 ml) and triethylamine (20 ml) in dichloromethane (30 ml) was added dropwise while cooling the mixture with an ice bath. The reaction mixture was stirred at ambient temperature for 16 hours. The mixture was concentrated and the residue was purified by column chromatography on silica gel (eluent: 10-55% v/v ethyl acetate in heptane) to give 3-hydroxy-2-nitro-benzoic acid methyl ester (15.9 g). 1H-NMR (400 MHz, CDCl$_3$): 10.15 (bs, 1H), 7.60 (t, 1H), 7.27 (d, 1H), 7.08 (d, 1H), 3.93 (s, 3H) ppm.

Example I4.2

Preparation of 4-bromo-3-hydroxy-2-nitro-benzoic acid methyl ester

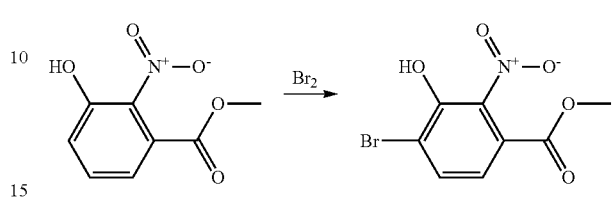

To a solution of 3-hydroxy-2-nitrobenzoic acid methyl ester (11 g) in chloroform (220 ml) was added dropwise bromine (18.7 g). The reaction mixture was heated at reflux for 16 hours. The reaction mixture was allowed to cool to ambient temperature and the reaction quenched by addition of aqueous sodium metabisulfite (22 g in 100 ml water) and the mixture was stirred for 15 minutes. The phases were separated and the organic phase was washed with brine, dried over sodium sulfate and concentrated. The residue was crystallized from diethyl ether/heptane to give 4-bromo-3-hydroxy-2-nitro-benzoic acid methyl ester (6.6 g). 1H-NMR (400 MHz, CDCl$_3$): 9.92 (s, 1H), 7.84 (d, 1H), 7.09 (d, 1H), 3.93 (s, 3H) ppm.

Example I4.3

Preparation of 2-amino-4-bromo-3-hydroxy-benzoic acid methyl ester

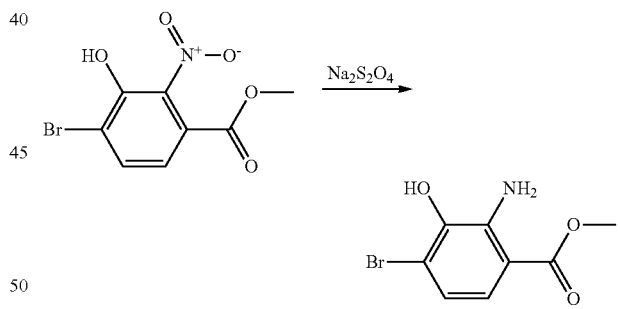

To a solution of 4-bromo-3-hydroxy-2-nitro-benzoic acid methyl ester (3.13 g) in tetrahydrofuran (40 ml) was added a solution of sodium dithionite (10.23 g) in water (40 ml).

The reaction mixture was stirred at 60° C. for 2 hours. Then the reaction was diluted with ethyl acetate (80 ml) and aqueous hydrochloric acid (1M) (30 ml) and the mixture vigorously shaken. The phases were separated and the aqueous phase was extracted with ethyl acetate (60 ml). The combined organic extracts were washed with brine, dried over sodium sulfate and concentrated to give 2-amino-4-bromo-3-hydroxy-benzoic acid methyl ester (2.46 g). 1H-NMR (400 MHz, CDCl$_3$): 7.35 (d, 1H), 6.72 (d, 1H), 6.05 (s, 1H), 5.47 (s, 1H), 3.87 (s, 3H) ppm.

Example I4.4

Preparation of 7-bromo-2-methyl-benzo[d]oxazole-4-carboxylic acid methyl ester

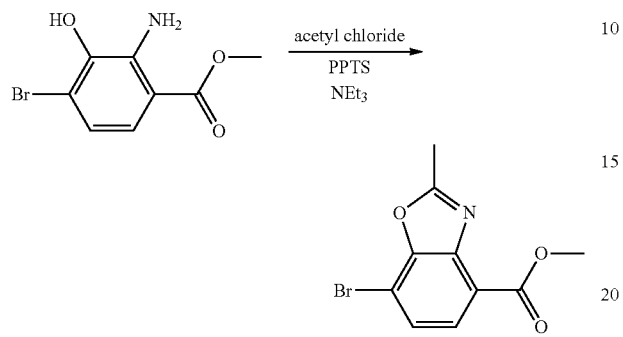

To a solution of 2-amino-4-bromo-3-hydroxy-benzoic acid methyl ester (2.46 g) in toluene (250 ml) was added sequentially triethylamine (1.53 ml), pyridinium p-toluenesulfonate ("PPTS") (0.75 g) and acetyl chloride (0.78 ml). The reaction mixture was heated at reflux for 16 hours. The reaction mixture was cooled to ambient temperature and diluted with aqueous hydrochloric acid (1M) (100 ml) and ethyl acetate (200 ml). The phases were separated and the organic extract was washed with aqueous hydrochloric acid (1M) (150 ml) and brine (150 ml) and then dried over sodium sulfate. The solids were removed by filtration and the filtrate was concentrated to give 7-bromo-2 methyl-benzo[d]oxazole-4-carboxylic acid methyl ester (2.94 g). 1H-NMR (400 MHz, CDCl$_3$): 7.87 (d, 1H), 7.52 (d, 1H), 4.04 (s, 3H), 2.77 (s, 3H) ppm.

Example I4.5

Preparation of (7-bromo-2-methyl-benzo[d]oxazol-4-yl)-methanol

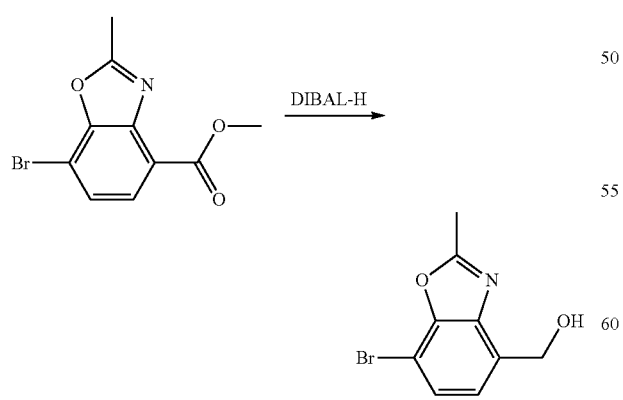

To a solution of 7-bromo-2 methyl-benzo[d]oxazole-4-carboxylic acid methyl ester (8.64 g) in tetrahydrofuran (250 ml) was added dropwise a solution of diisobutylaluminium hydride ("DIBAL-H") (1M in hexane) (80 ml) under a nitrogen atmosphere at 0° C. The reaction mixture was stirred at 0° C. for 20 minutes. Then the ice-bath was removed and the reaction mixture was allowed to warm to ambient temperature. After 40 minutes the mixture was cooled with an ice-bath and the reaction was quenched by the slow addition of water (5.0 ml). The mixture was poured onto aqueous sodium hydrogen carbonate (saturated) (300 ml) and extracted with diethyl ether (400 ml). The aqueous phase was further extracted with diethyl ether (2×300 ml). The combined organic extracts were washed with brine, dried over sodium sulfate and concentrated. The residue was triturated in a mixture of diisopropyl ether and heptane (3:1) to give (7-bromo-2-methyl-benzo[d]oxazol-4-yl)-methanol (4.45 g). 1H-NMR (400 MHz, CDCl$_3$): 7.41 (d, 1H), 7.17 (d, 1H), 4.98 (s, 3H), 3.06 (s, 1H), 2.67 (s, 3H) ppm.

Example I4.6

Preparation of 7-bromo-2-methyl-benzo[d]oxazole-4-carbaldehyde

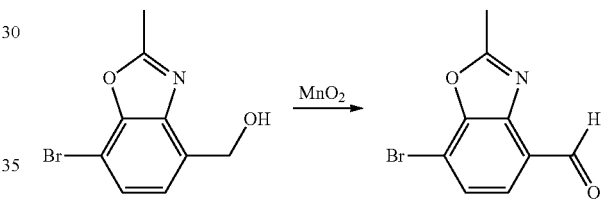

To a solution of (7-bromo-2-methyl-benzo[d]oxazol-4-yl) methanol (5.16 g) in dichloromethane (300 ml) was added manganese(IV) oxide (59.9 g) and the suspension stirred at ambient temperature for 16 hours. The reaction mixture was filtered through a plug of silica gel and the filtrate concentrated to give 7-bromo-2-methyl-benzo[d]oxazole-4-carbaldehyde (3.23 g). LC-MS: R$_T$=1.83 min, [M+H]$^+$=240.0/242.0, using the following method:

Method (Agilent 1100er Series) with the following HPLC gradient conditions (Solvent A: 0.05% formic acid in water; Solvent B: 0.04% formic acid in acetonitrile).

| Time (minutes) | A (%) | B (%) | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |

Type of column: Phenomenex Gemini C18; Column length: 30 mm, Internal diameter of column 3 mm, Particle size 3 micron; Temperature 60° C.

The characteristics obtained for each compound were the retention time ("RT" recorded in minutes) and the molecular ion MH$^+$.

Example I4.7

Preparation of (E)-7-bromo-2-methyl-benzo[d]oxazole-4-carbaldehyde oxime

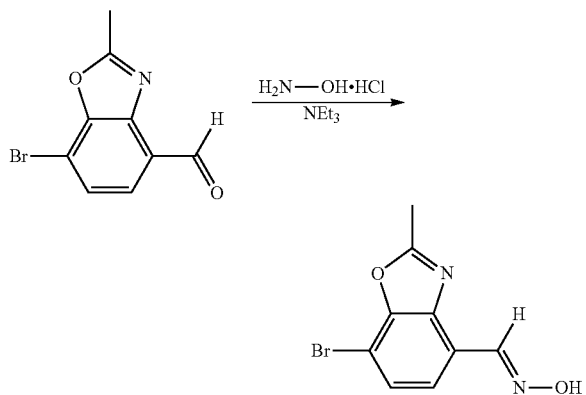

To a suspension of 7-bromo-2-methyl-benzo[d]oxazole-4-carbaldehyde (3.23 g) in a mixture of methanol and water (7:3) (60 ml) were added successively hydroxylamine hydrochloride (1.03 g) and triethylamine (2.06 ml) and the reaction mixture was stirred at ambient temperature for 1 hour. The reaction mixture was diluted with ethyl acetate (200 ml) and water (200 ml). The phases were separated and the aqueous phase was extracted with ethyl acetate (150 ml). The combined organic extracts were washed with brine (200 ml), dried over sodium sulfate and concentrated to give (E)-7-bromo-2-methyl-benzo[d]oxazole-4-carbaldehyde oxime (3.61 g) as a brown solid. 1H-NMR (400 MHz, CDCl$_3$): 9.47 (s, 1H) 7.47 (d, 1H), 7.33 (d, 1H), 2.74 (s, 3H) ppm.

Example I4.8

Preparation of (Z)-7-bromo-N-hydroxy-2-methyl-benzo[d]oxazole-4-carbimidoyl chloride

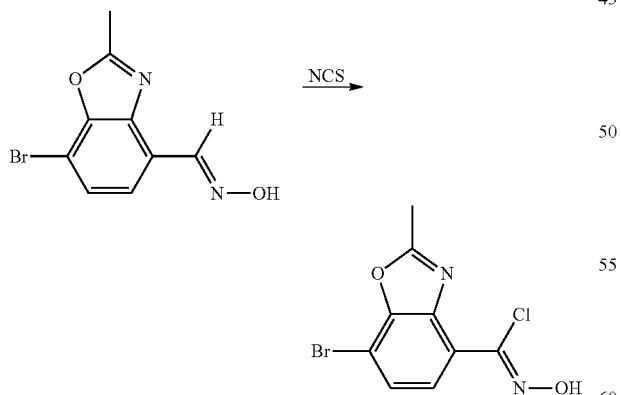

To a solution of (E)-7-bromo-2-methyl-benzo[d]oxazole-4-carbaldehyde oxime (3.61 g) in dimethylformamide (30 ml) was added N-bromosuccinimide ("NCS") (7.54 g) and the reaction mixture stirred at ambient temperature for two hours. Water (300 ml) was added to the mixture and the solids were isolated by filtration to give (Z)-7-bromo-N-hydroxy-2-methyl-benzo[d]oxazole-4-carbimidoyl chloride (3.63 g) as an orange solid. 1H-NMR (DMSO-d6, 400 MHz): 12.76 (s, 1H) 7.69 (d, 1H), 7.58 (d, 1H), 2.68 (s, 3H) ppm.

Example I4.9

Preparation of 7-bromo-4-(5-(3,5-dichlorophenyl)-5-trifluoromethyl-4,5-dihydro-isoxazol-3-yl)-2-methyl-benzo[d]oxazole

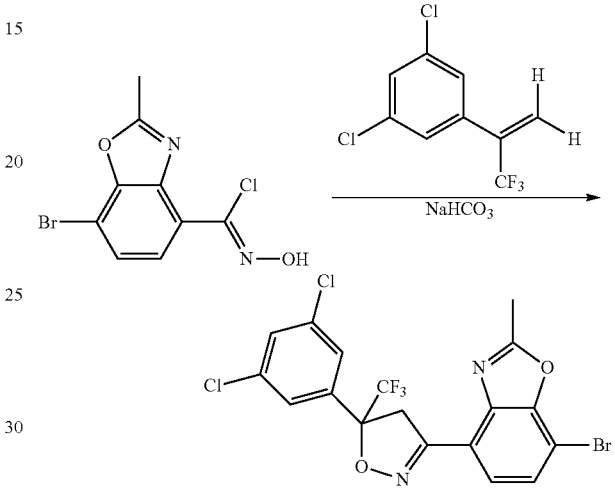

To a solution of 7-bromo-N-hydroxy-2-methyl-benzo[d]oxazole-4-carbimidoyl chloride (3.63 g) in 2-propanol (100 ml) was added 1,3-dichloro-5-(1-trifluoromethyl-vinyl)-benzene (preparation described in, for example, EP 1,731,512) (3.43 g) and sodium hydrogen carbonate (1.44 g). The reaction mixture was stirred at 65° C. for 16 hours. The reaction mixture was concentrated and the residue was purified by column chromatography on silica gel (eluent: 2-25% v/v ethyl acetate in heptane) to give 7-bromo-4-(5-(3,5-dichlorophenyl)-5-trifluoromethyl-4,5-dihydro-isoxazol-3-yl)-2-methyl-benzo[d]oxazole (3.7 g). 1H-NMR (400 MHz, CDCl$_3$): 7.71-7.42 (m, 5H), 4.50 (d, 1H), 4.06 (d, 1H), 2.73 (s, 3H) ppm.

Example I4.10

Preparation of 4-(5-(3,5-dichlorophenyl)-5-trifluoromethyl-4,5-dihydro-isoxazol-3-yl)-2-methyl-benzo[d]oxazole-7-carboxylic acid methyl ester

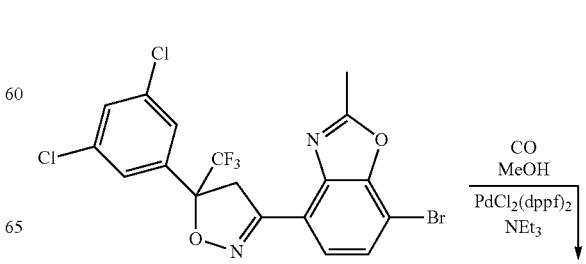

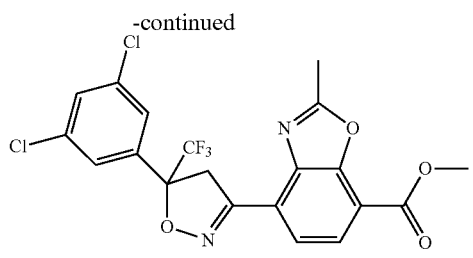

To a solution of 7-bromo-4-(5-(3,5-dichlorophenyl)-5-trifluoromethyl-4,5-dihydro-isoxazol-3-yl)-2-methyl-benzo[d]oxazole (3.5 g) in dimethylformamide (40 ml) was added successively triethylamine (2.5 ml), methanol (60 ml) and [1,1'-bis(diphenylphosphino)ferrocene]dichloropalladium (II) ("PdC12(dppf)") (259 mg). The reaction mixture was stirred in a pressure reactor in an atmosphere of carbon monoxide (4 bar) at 80° C. for 16 hours. The reaction mixture was cooled to ambient temperature, filtered over a plug of Celite® and concentrated. The residue was purified by column chromatography on silica gel (eluent: 15-55% v/v ethyl acetate in heptane) to give 4-(5-(3,5-dichlorophenyl)-5-trifluoromethyl-4,5-dihydro-isoxazol-3-yl)-2-methyl-benzo[d]oxazole-7-carboxylic acid methyl ester (2.75 g). 1H-NMR (400 MHz, CDCl$_3$): 7.95-7.42 (m, 5H), 4.56 (d, 1H), 4.12 (d, 1H), 4.02 (s, 3H), 2.77 (s, 3H) ppm.

Example I4.11

Preparation of 4-(5-(3,5-dichlorophenyl)-5-trifluoromethyl-4,5-dihydro-isoxazol-3-yl)-2-methyl-benzo[d]oxazole-7-carboxylic acid

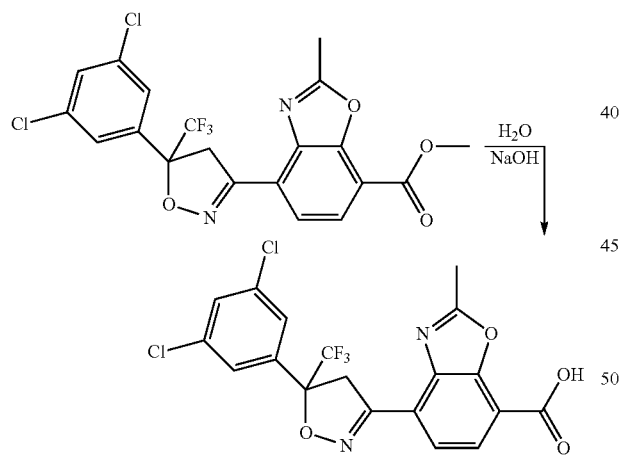

To a solution of 4-(5-(3,5-dichlorophenyl)-5-trifluoromethyl-4,5-dihydro-isoxazol-3-yl)-2-methyl-benzo[d]oxazole-7-carboxylic acid methyl ester (2.75 g) in tetrahydrofuran (50 ml) was added aqueous sodium hydroxide (1M) (8.7 ml) and methanol (5 ml). The reaction mixture was stirred at ambient temperature for 2.5 hours. The reaction mixture was diluted with aqueous hydrochloric acid (1M) (150 ml) and ethyl acetate (200 ml) and the phases separated. The organic phase was washed with brine, dried over sodium sulfate and concentrated. The residue was purified by column chromatography on silica gel (eluent: 1-6% v/v methanol in dichloromethane) to give 4-(5-(3,5-dichlorophenyl)-5-trifluoromethyl-4,5-dihydro-isoxazol-3-yl)-2-methyl-benzo[d]oxazole-7-carboxylic acid (2.12 g) as yellow solid. 1H-NMR (400 MHz, CDCl$_3$): 8.05-7.43 (m, 5H), 4.57 (d, 1H), 4.13 (d, 1H), 2.79 (s, 3H) ppm.

Example P4

General Method for Preparing the Compounds of the Invention in Parallel

To a solution of the carboxylic acid (30 μmol) in dimethylacetamide (0.4 ml) was added a solution of the amine (30 μmol) in dimethylacetamide (0.145 ml) followed by diisopropylethylamine (Hunig's Base) (0.02 ml, 100 μmol) and a solution of bis(2-oxo-3-oxazolidinyl)phosphonic chloride ("BOP-Cl") (15.3 mg) in dimethylacetamide (0.2 ml). The reaction mixture was stirred at 80° C. for 16 hours. Then the mixture was diluted with acetonitrile (0.6 ml) and a sample was used for the LC-MS analysis. The remaining mixture was further diluted with acetonitrile/dimethylformamide (4:1) (0.8 ml) and purified by HPLC to give the desired compound.

The following method was used for HPLC-MS analysis:

Method (Agilent 1100er Series) with the following HPLC gradient conditions (Solvent A: 0.1% formic acid in water; Solvent B: 0.1% formic acid in acetonitrile).

| Time (minutes) | A (%) | B (%) | Flow (ml/min) |
| --- | --- | --- | --- |
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

Type of column: Waters Atlantis dc18; Column length: 20 mm, Internal diameter of column 3 mm, Particle size 3 micron; Temperature 40° C.

The characteristics obtained for each compound were the retention time ("RT" recorded in minutes) and the molecular io, typically the cation MH$^+$ as listed in Table E.

TABLE E

Compounds of formula Ih

[Structure Ih shown]

| Comp No. | R¹ | R² | RT (min) | MH⁺ |
|---|---|---|---|---|
| E1 | [3-sulfonyl-oxetanyl] | H | 3.47 | 562 |
| E2 | [3-methyl-3-thietanyl] | H | 4.12 | 544 |
| E3 | [3-sulfinyl-oxetanyl] | H | 3.18 | 546 |
| E4 | [3-thietanyl] | H | 3.91 | 530 |

Biological Examples

This Example illustrates the pesticidal/insecticidal properties of compounds of formula (I). Tests were performed as follows:

*Spodoptera littoralis* (Egyptian cotton leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compound gave at least 80% control of *Spodoptera littoralis*: A2, A3, A5, A6, A13, A19, A20, A22, A24.

*Heliothis virescens* (Tobacco budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compound gave at least 80% control of *Heliothis virescens*: A12, A13, A21, A22, A24.

*Plutella xylostella* (Diamond back moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compound gave at least 80% control of *Plutella xylostella*: A1, A2, A3, A4, A5, A6.

*Diabrotica balteata* (Corn root worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compound gave at least 80% control of *Diabrotica balteata*: A9, A13, A21, A22, A23, A24.

*Thrips tabaci* (Onion thrips):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality. The following compounds gave at least 80% control of *Thrips tabaci*: A13, A22.

The invention claimed is:

1. A compound of formula (I)

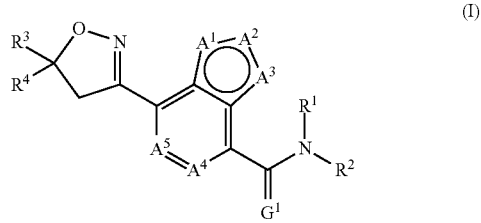

wherein
$A^1$, $A^2$ and $A^3$ are independently C—$R^5$, nitrogen, N—$R^6$, oxygen or sulfur, provided that two of $A^1$, $A^2$ or $A^3$ are C—$R^5$ or nitrogen and that one of $A^1$, $A^2$ or $A^3$ is N—$R^6$, oxygen or sulfur;
$A^4$ and $A^5$ are independently C—$R^5$ or nitrogen;
$G^1$ is oxygen or sulfur;
$R^1$ is hydrogen, $C_1$-$C_8$alkyl, $C_1$-$C_8$alkylcarbonyl-, or $C_1$-$C_8$alkoxycarbonyl-;
$R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one to five $R^8$, aryl-$C_1$-$C_4$alkylene- or aryl-$C_1$-$C_4$alkylene- wherein the aryl moiety is substituted by one to five $R^9$, heterocyclyl-$C_1$-$C_4$alkylene- or heterocyclyl-$C_1$-$C_4$alkylene- wherein the heterocyclyl moiety is substituted by one to five $R^9$, aryl or aryl substituted by one to five $R^9$, heterocyclyl or heterocyclyl substituted by one to five $R^9$, $C_1$-$C_8$alkylaminocarbonyl-$C_1$-$C_4$alkylene, $C_1$-$C_8$haloalkylaminocarbonyl-$C_1$-$C_4$alkylene, or $C_3$-$C_8$cycloalkyl-aminocarbonyl-$C_1$-$C_4$alkylene;
$R^3$ is $C_1$-$C_8$haloalkyl;
$R^4$ is aryl or aryl substituted by one to five $R^{10}$, or heteroaryl or heteroaryl substituted by one to five $R^{10}$;
each $R^5$ is independently hydrogen, halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^6$ is independently hydrogen or $C_1$-$C_8$alkyl;

each $R^7$ is independently halogen, cyano, nitro, hydroxy, $C_1$-$C_8$alkoxy, $C_1$-$C_8$haloalkoxy, mercapto, $C_1$-$C_8$alkylthio-, $C_1$-$C_8$haloalkylthio-; $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^8$ is independently halogen or $C_1$-$C_8$alkyl;

each $R^9$ and $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{11}$, or heterocyclyl or heterocyclyl substituted by one to five $R^{11}$; and each $R^{11}$ is independently halogen, cyano, nitro, $C_1$-$C_4$alkyl, $C_1$-$C_4$haloalkyl, $C_1$-$C_4$alkoxy, or $C_1$-$C_4$haloalkoxy; or a salt or N-oxide thereof;

provided that -$A^1$-$A^2$-$A^3$- is not —O—(CR$^5$)=N—, —S—(CR$^5$)=N—, N=(CR$^5$)—O— or —N=(CR$^5$)—S— irrespective of the values for $A^4$ and $A^5$, and provided that -$A^1$-$A^2$-$A^3$- is not —(CR$^5$)=(CR$^5$)—O—, —O—(CR$^5$)=(CR$^5$)—, —(CR$^5$)=(CR$^5$)—S—, —S—(CR$^5$)=(CR$^5$)—, —(CR$^5$)=(CR$^5$)—(NR$^6$)—, —(NR$^6$)—(CR$^5$)=(CR$^5$)—, —(CR$^5$)=N—(NR$^6$)— and —(NR$^6$)—N=(CR$^5$)— when $A^4$ and $A^5$ are both C—R$^5$.

2. A compound according to claim 1 wherein $A^1$ and $A^3$ are nitrogen or N—R$^6$ and $A^2$ is C—R$^5$, N—R$^6$, nitrogen or sulfur.

3. A compound according to claim 1 wherein -$A^1$-$A^2$-$A^3$- is selected from =N—S—N=, —N=C(R$^5$)—N(R$^6$)—, —N(R$^6$)—C(R$^5$)=N—, =N—N(R$^6$)—N=, —N=N—N(R$^6$)— and —N(R$^6$)—N=N—.

4. A compound according to claim 1 wherein $A^4$ and $A^5$ are C—R$^5$.

5. A compound according to claim 1 wherein $G^1$ is oxygen.

6. A compound according to claim 1 wherein $R^1$ is hydrogen, methyl, ethyl, methylcarbonyl-, or methoxycarbonyl-.

7. A compound according to claim 1 wherein $R^2$ is $C_1$-$C_8$alkyl or $C_1$-$C_8$alkyl substituted by one to five $R^7$, $C_3$-$C_{10}$cycloalkyl or $C_3$-$C_{10}$cycloalkyl substituted by one to five $R^8$, phenyl-$C_1$-$C_4$alkylene- or phenyl-$C_1$-$C_4$alkylene- wherein the phenyl moiety is substituted by one to four $R^9$, pyridyl-$C_1$-$C_4$alkylene- or pyridyl-$C_1$-$C_4$alkylene- wherein the pyridyl moiety is substituted by one to four $R^9$, oxetanyl or oxetanyl substituted by one to five $R^9$, thietanyl or thietanyl substituted by one to five $R^9$, oxo-thietanyl or oxo-thietanyl substituted by one to five $R^9$, or dioxo-thietanyl or dioxo-thietanyl substituted by one to five $R^9$.

8. A compound according to claim 1 wherein $R^3$ is chlorodifluoromethyl or trifluoromethyl.

9. A compound according to claim 1 wherein $R^4$ is aryl or aryl substituted by one to five $R^{10}$.

10. A compound according to claim 1 wherein
$A^1$ and $A^3$ are nitrogen or N—R$^6$ and $A^2$ is C—R$^5$, N—R$^6$, nitrogen or sulfur, provided that two of $A^1$, $A^2$ or $A^3$ are C—R$^5$ or nitrogen and that one of $A^1$, $A^2$ or $A^3$ is N—R$^6$ or sulfur;

$A^4$ and $A^5$ are CH;

$G^1$ is oxygen;

$R^1$ is hydrogen, methyl or ethyl;

$R^2$ is $C_1$-$C_8$alkyl or $C_1$-$C_8$alkyl substituted by one to five $R^7$, $C_3$-$C_{10}$cycloalkyl or $C_3$-$C_{10}$ cycloalkyl substituted by one to five $R^8$, phenyl-$C_1$-$C_4$alkylene- or phenyl-$C_1$-$C_4$alkylene- wherein the phenyl moiety is substituted by one to five $R^9$, pyridyl-$C_1$-$C_4$alkylene- or pyridyl-$C_1$-$C_4$alkylene- wherein the pyridyl moiety is substituted by one to four $R^9$, imidazolyl-$C_1$-$C_4$alkylene or imidazolyl-$C_1$-$C_4$alkylene wherein the imidazolyl moiety is substituted by one to five $R^9$, oxetanyl or oxetanyl substituted by one to five $R^9$, thietanyl or thietanyl substituted by one to five $R^9$, oxo-thietanyl or oxo-thietanyl substituted by one to five $R^9$, dioxo-thietanyl or dioxo-thietanyl substituted by one to five $R^9$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene;

$R^3$ is chlorodifluoromethyl or trifluoromethyl;

$R^4$ is 3,5-dibromo-phenyl-, 3,5-dichloro-phenyl-, 3,4-dichloro-phenyl-, 4-bromo-3,5-dichloro-phenyl or 3,4,5-trichloro-phenyl-;

$R^5$ is independently hydrogen, bromo, chloro, fluoro, cyano, nitro, methyl, ethyl, trifluoromethyl, methoxy, difluoromethoxy, or trifluoromethoxy;

$R^6$ is hydrogen, methyl or ethyl;

each $R^7$ is independently bromo, chloro, fluoro, methyl, methoxy, or methylthio;

each $R^8$ is methyl;

each $R^9$ is independently bromo, chloro, fluoro, cyano, nitro, methyl, ethyl, trifluoromethyl, methoxy, difluoromethoxy, or trifluoromethoxy.

11. A compound according to claim 1 wherein
-$A^1$-$A^2$-$A^3$- is selected from =N—S—N=, —N=C(R$^5$)—N(R$^6$)—, —N(R$^6$)—C(R$^5$)=N—, =N—N(R$^6$)—N=, —N=N—N(R$^6$)— and —N(R$^6$)—N=N—;

$A^4$ and $A^5$ are CH;

$G^1$ is oxygen;

$R^1$ is hydrogen;

$R^2$ is $C_1$-$C_8$alkyl or $C_1$-$C_8$alkyl substituted by one to five $R^7$, $C_3$-$C_{10}$cycloalkyl or $C_3$-$C_{10}$ cycloalkyl substituted by one or two methyl groups, phenyl-$C_1$-$C_4$alkylene- or phenyl-$C_1$-$C_4$alkylene- wherein the phenyl moiety is substituted by one to five $R^9$, pyridyl-$C_1$-$C_4$alkylene- or pyridyl-$C_1$-$C_4$alkylene- wherein the pyridyl moiety is substituted by one to four $R^9$, imidazolyl-$C_1$-$C_4$alkylene or imidazolyl-$C_1$-$C_4$alkylene wherein the imidazolyl moiety is substituted by one to five $R^9$, oxetanyl or oxetanyl substituted by one to five $R^9$, thietanyl or thietanyl substituted by one to five $R^9$, oxo-thietanyl or oxo-thietanyl substituted by one to five $R^9$, dioxo-thietanyl or dioxo-thietanyl substituted by one to five $R^9$;

$R^3$ is trifluoromethyl;

$R^4$ is 3,5-dichloro-phenyl;

$R^5$ is hydrogen or methyl;

$R^6$ is hydrogen or methyl;

each $R^7$ is independently bromo, chloro, fluoro, methoxy, or methylthio;

each $R^9$ is independently bromo, chloro, fluoro, nitro, or methyl.

12. A method of combating and/or controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

13. An insecticidal, acaricidal, nematicidal or molluscicidal composition comprising an insecticidally, acaricidally, nematicidally or molluscicidally effective amount of a compound of formula (I) as defined in claim 1.

14. An insecticidal, acaricidal, nematicidal or molluscicidal composition according to claim 13 comprising an additional compound having biological activity.

15. A compound of formula (A)

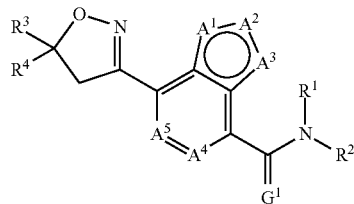

(A)

wherein $A^1$, $A^2$ and $A^3$ are independently C—$R^5$, nitrogen, N—$R^6$, oxygen or sulfur, provided that two of $A^1$, $A^2$ or $A^3$ are C—$R^5$ or nitrogen and that one of $A^1$, $A^2$ or $A^3$ is N—$R^6$, oxygen or sulfur;

$A^4$ and $A^5$ are independently C—$R^5$ or nitrogen;

$G^1$ is oxygen or sulfur;

$R^1$ is hydrogen, $C_1$-$C_8$alkyl, $C_1$-$C_8$alkylcarbonyl-, or $C_1$-$C_8$alkoxycarbonyl-;

$R^2$ is cyclobutyl or cyclobutyl substituted by one to five $R^8$, oxetanyl or oxetanyl substituted by one to five $R^9$, thietanyl or thietanyl substituted by one to five $R^9$, oxo-thietanyl or oxo-thietanyl substituted by one to five $R^9$, or dioxo-thietanyl or dioxo-thietanyl substituted by one to five $R^9$;

$R^3$ is $C_1$-$C_8$haloalkyl;

$R^4$ is aryl or aryl substituted by one to five $R^{10}$, or heteroaryl or heteroaryl substituted by one to five $R^{10}$;

each $R^5$ is independently hydrogen, halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^6$ is independently hydrogen or $C_1$-$C_8$alkyl;

each $R^8$ is independently halogen or $C_1$-$C_8$alkyl;

each $R^9$ and $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{11}$, or heterocyclyl or heterocyclyl substituted by one to five $R^{11}$; and each $R^{11}$ is independently halogen, cyano, nitro, $C_1$-$C_4$alkyl, $C_1$-$C_4$haloalkyl, $C_1$-$C_4$alkoxy, or $C_1$-$C_4$haloalkoxy; or a salt or N-oxide thereof.

16. A compound according to claim 15, wherein

-$A^1$-$A^2$-$A^3$- is selected from =N—S—N=, —S—N=N—, —N=N—S—, =N—N($R^6$)—N=, —N=N—N($R^6$)—, —N($R^6$)—N=N—, —C($R^5$)=N—N($R^6$)—, —N($R^6$)—N=C($R^5$)—, —N=C($R^5$)—N($R^6$)—, —N($R^6$)—C($R^5$)=N—, —N=C($R^5$)—O— and —O—C($R^5$)=N—;

$A^4$ and $A^5$ are independently CH or nitrogen;

$G^1$ is oxygen;

$R^1$ is hydrogen, methyl, ethyl, methylcarbonyl-, or methoxycarbonyl-;

$R^2$ is cyclobutyl or cyclobutyl substituted by one to five $R^8$, oxetanyl or oxetanyl substituted by one to five $R^9$, thietanyl or thietanyl substituted by one to five $R^9$, oxo-thietanyl or oxo-thietanyl substituted by one to five $R^9$, or dioxo-thietanyl or dioxo-thietanyl substituted by one to five $R^9$;

$R^3$ is $C_1$-$C_8$haloalkyl;

$R^4$ is phenyl substituted by two to three $R^{10}$;

$R^5$ is hydrogen, bromo, chloro, fluoro, cyano, nitro, methyl, ethyl, trifluoromethyl, methoxy, difluoromethoxy, or trifluoromethoxy;

$R^6$ is hydrogen or $C_1$-$C_8$alkyl;

each $R^8$ is independently chloro, fluoro or methyl;

each $R^9$ is independently halogen, cyano, nitro, $C_1$-$C_8$alkyl, $C_1$-$C_8$haloalkyl, $C_1$-$C_8$alkoxy, $C_1$-$C_8$haloalkoxy;

each $R^{10}$ is independently halogen, $C_1$-$C_8$alkoxy, $C_1$-$C_8$haloalkoxy, $C_1$-$C_8$alkylthio-, or $C_1$-$C_8$haloalkylthio-.

\* \* \* \* \*